US012653597B2

(12) United States Patent
Viswanathan

(10) Patent No.: US 12,653,597 B2
(45) Date of Patent: *Jun. 16, 2026

(54) APPARATUS, SYSTEMS AND METHODS FOR SOFT TISSUE ABLATION

(71) Applicant: Alpfa Medical, Inc., Menlo Park, CA (US)

(72) Inventor: Raju Viswanathan, Palo Alto, CA (US)

(73) Assignee: Alpfa Medical, Inc., Menlo Park, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 19/325,396

(22) Filed: Sep. 10, 2025

(65) Prior Publication Data

US 2026/0007448 A1    Jan. 8, 2026

Related U.S. Application Data

(60) Continuation of application No. 19/172,274, filed on Apr. 7, 2025, now Pat. No. 12,426,933, which is a
(Continued)

(51) Int. Cl.
*A61B 18/12* (2006.01)
*A61B 18/00* (2006.01)

(52) U.S. Cl.
CPC .... *A61B 18/00* (2013.01); *A61B 2018/00577* (2013.01); *A61B 2018/00613* (2013.01);
(Continued)

(58) Field of Classification Search
CPC . A61B 18/00; A61B 18/1206; A61B 18/1492; A61B 2018/00577;
(Continued)

(56) References Cited

U.S. PATENT DOCUMENTS 9,233,241 B2 * 1/2016 Long ................. A61B 18/1492
9,987,081 B1 6/2018 Bowers et al.
(Continued)

FOREIGN PATENT DOCUMENTS

WO    WO-2023239966 A1    12/2023
WO    WO-2024211752 A1    10/2024
WO    WO-2025160398 A2    7/2025

OTHER PUBLICATIONS

Aycock, K. N. et al., "A Theoretical Argument for Extended Interpulse Delays in Therapeutic High-Frequency Irreversible Electroporation Treatments," IEEE Transactions on Biomedical Engineering, vol. 68, No. 6 (Jan. 2021), pp. 1999-2010.
(Continued)

*Primary Examiner* — Michael F Peffley
(74) *Attorney, Agent, or Firm* — COOLEY LLP

(57) ABSTRACT

Systems, devices, and methods described herein relate to generation and delivery of pulsed waveforms, e.g., for therapy delivery in soft tissue ablation procedures. In some embodiments, a pulse generator is configured to generate a voltage pulse train including a plurality of biphasic pulses, each biphasic pulse of the plurality of biphasic pulses including a positive pulse, a negative pulse, and an interphase delay separating the positive pulse and the negative pulse. In some embodiments, successive biphasic pulses of the plurality of biphasic pulses can be separated by a pulse-to-pulse delay such that the plurality of biphasic pulses is separated by a plurality of pulse-to-pulse delays, and the plurality of pulse-to-pulse delays can include increasing or decreasing sequences of pulse-to-pulse delays.

30 Claims, 23 Drawing Sheets

Related U.S. Application Data division of application No. 18/976,095, filed on Dec. 10, 2024, now Pat. No. 12,446,943, which is a continuation-in-part of application No. PCT/US2023/025064, filed on Jun. 12, 2023.

(60) Provisional application No. 63/351,197, filed on Jun. 10, 2022.

(52) U.S. Cl.
CPC .............. *A61B 2018/00761* (2013.01); *A61B 2018/00767* (2013.01)

(58) Field of Classification Search
CPC ........... A61B 2018/00613; A61B 2018/00726; A61B 2018/00761; A61B 2018/00767; A61B 2018/124; A61B 2018/1427; A61B 2018/143; A61B 2018/1475; A61N 1/327
See application file for complete search history.

(56) References Cited

U.S. PATENT DOCUMENTS

| | | | |
|---|---|---|---|
| 10,322,286 B2 | 6/2019 | Viswanathan et al. | |
| 10,342,598 B2 | 7/2019 | Long et al. | |
| 10,448,989 B2 | 10/2019 | Arena et al. | |
| 10,512,505 B2 * | 12/2019 | Viswanathan | A61B 18/1492 |
| 10,569,081 B2 | 2/2020 | Howard | |
| 10,709,502 B2 * | 7/2020 | Viswanathan | A61B 18/1492 |
| 10,813,688 B2 | 10/2020 | Pearson et al. | |
| 10,828,086 B2 | 11/2020 | Davalos et al. | |
| 11,254,926 B2 | 2/2022 | Neal, II et al. | |
| 11,278,349 B2 | 3/2022 | Stewart et al. | |
| 11,540,877 B2 | 1/2023 | Altmann et al. | |
| 11,547,851 B2 | 1/2023 | Krimsky et al. | |
| 11,655,466 B2 | 5/2023 | Neal et al. | |
| 11,701,169 B2 | 7/2023 | Stewart et al. | |
| 12,076,072 B2 | 9/2024 | Athos et al. | |
| 12,102,374 B2 | 10/2024 | Altmann et al. | |
| 12,150,700 B2 | 11/2024 | Stewart et al. | |
| 12,150,701 B2 | 11/2024 | Stewart et al. | |
| 12,201,353 B2 | 1/2025 | Stewart et al. | |
| 12,207,866 B2 | 1/2025 | Stewart et al. | |
| 12,390,272 B2 | 8/2025 | Mickelsen | |
| 12,408,979 B2 | 9/2025 | Mickelsen | |
| 12,426,933 B2 | 9/2025 | Viswanathan | |
| 12,446,943 B2 | 10/2025 | Viswanathan et al. | |
| 12,485,279 B2 | 12/2025 | Aycock et al. | |
| 12,521,055 B2 | 1/2026 | Pederson et al. | |
| 2022/0022952 A1 | 1/2022 | Koop et al. | |
| 2022/0104875 A1 * | 4/2022 | Gleiman | A61B 18/16 |
| 2022/0161027 A1 * | 5/2022 | Aycock | A61N 1/0416 |
| 2022/0257297 A1 | 8/2022 | Koop et al. | |
| 2022/0361944 A1 | 11/2022 | McNern et al. | |
| 2023/0172650 A1 * | 6/2023 | Castellvi | A61B 18/1492 606/32 |
| 2023/0200893 A1 | 6/2023 | Strong | |
| 2023/0346460 A1 | 11/2023 | Govari et al. | |
| 2023/0389984 A1 | 12/2023 | Redjebian | |
| 2024/0299076 A1 | 9/2024 | O'Brien et al. | |
| 2025/0099151 A1 | 3/2025 | Viswanathan | |
| 2025/0205481 A1 | 6/2025 | Davalos et al. | |
| 2025/0213299 A1 | 7/2025 | Nafie et al. | |
| 2025/0221757 A1 | 7/2025 | Byrd et al. | |
| 2025/0228597 A1 | 7/2025 | Viswanathan | |
| 2025/0281217 A1 | 9/2025 | Mittal et al. | |

OTHER PUBLICATIONS

International Application No. PCT/US2023/025064, International Preliminary Report on Patentability mailed Dec. 19, 2024; Applicant: Alpfa Medical, Inc.; 12 pages.

International Application No. PCT/US2023/025064, International Search Report and Written Opinion mailed Nov. 23, 2023; Applicant: Squirrel Corporation; 15 pages.

International Application No. PCT/US2023/025064, Invitation to Pay Additional Fees, dated Oct. 2, 2023; Applicant: Squirrel Corporation; 15 pages.

U.S. Appl. No. 18/976,095, Office Action mailed Apr. 18, 2025; Inventor: Viswanathan, Raju; 8 pages.

U.S. Appl. No. 19/172,274, Office Action mailed May 8, 2025; Inventor: Viswanathan, Raju; 9 pages.

* cited by examiner

| Pulse Number | Electrodes | Pulse-to-pulse delay |
|---|---|---|
| P1 | EP1({E1}, {E2}) | D1 |
| P2 | EP2({E1}, {E2}) | D2 |
| ⋮ | ⋮ | ⋮ |
| PN | EPN({EX}, {EY}) | DX |

FIG. 18

| Pulse Number | Electrodes | Pulse-to-pulse delay |
|---|---|---|
| P1 | ((E1), (E2)) | D1 |
| P2 | ((E1), (E2)) | D2 |
| P3 | ((E1), (E2)) | D3 |
| P4 | ((E1), (E2)) | D4 |
| P5 | ((E1), (E2)) | D5 |
| P6 | ((E1), (E2)) | D5 |
| P7 | ((E1), (E2)) | D4 |
| P8 | ((E1), (E2)) | D3 |
| P9 | ((E1), (E2)) | D2 |
| P10 | ((E1), (E2)) | D1 |
| P11 | ((E1), (E2)) | D6 |
| P12 | ((E1), (E2)) | D1 |
| : | : | : |
| : | : | : |
| PN | ((E1), (E2)) | - |

FIG. 19

| Pulse Number | Electrodes | Pulse-to-pulse delay |
| --- | --- | --- |
| P1 | ({E1}, {E2}) | D1 |
| P2 | ({E1}, {E2}) | D2 |
| P3 | ({E1}, {E2}) | D3 |
| P4 | ({E1}, {E2}) | D4 |
| P5 | ({E1}, {E2}) | D5 |
| P6 | ({E1}, {E2}) | D6 |
| P7 | ({E1}, {E3}) | D6 |
| P8 | ({E1}, {E3}) | D5 |
| P9 | ({E1}, {E3}) | D4 |
| P10 | ({E1}, {E3}) | D3 |
| P11 | ({E1}, {E3}) | D2 |

| Pulse Number | Electrodes | Pulse-to-pulse delay |
| --- | --- | --- |
| P12 | ({E1}, {E3}) | D1 |
| P13 | ({E1}, {E3}) | D1 |
| P14 | ({E2}, {E3}) | D2 |
| P15 | ({E2}, {E3}) | D3 |
| P16 | ({E2}, {E3}) | D4 |
| P17 | ({E2}, {E3}) | D5 |
| P18 | ({E2}, {E3}) | D6 |
| P19 | ({E2}, {E3}) | D6 |
| P20 | ({E2}, {E3}) | D7 |
| ... | ... | ~ |
| PN | ({EX}, {EY}) | - |

FIG. 20

| Pulse Number | Electrodes | Pulse-to-pulse delay |
|---|---|---|
| P1 | ({E1}, {E2}) | D1 |
| P2 | ({E3}, {E4}) | D2 |
| P3 | ({E1}, {E2}) | D3 |
| P4 | ({E2}, {E4}) | D4 |
| P5 | ({E1}, {E3}) | D5 |
| P6 | ({E1}, {E3}) | D6 |
| P7 | ({E2}, {E4}) | D7 |
| P8 | ({E3}, {E4}) | D8 |
| P9 | ({E1}, {E3}) | D9 |
| P10 | ({E1}, {E2}) | D10 |
| P11 | ({E2}, {E4}) | D11 |
| P12 | ({E3}, {E4}) | D12 |
| ... | ... | ... |
| PN | ({EX}, {EY}) | ~ |

FIG. 21

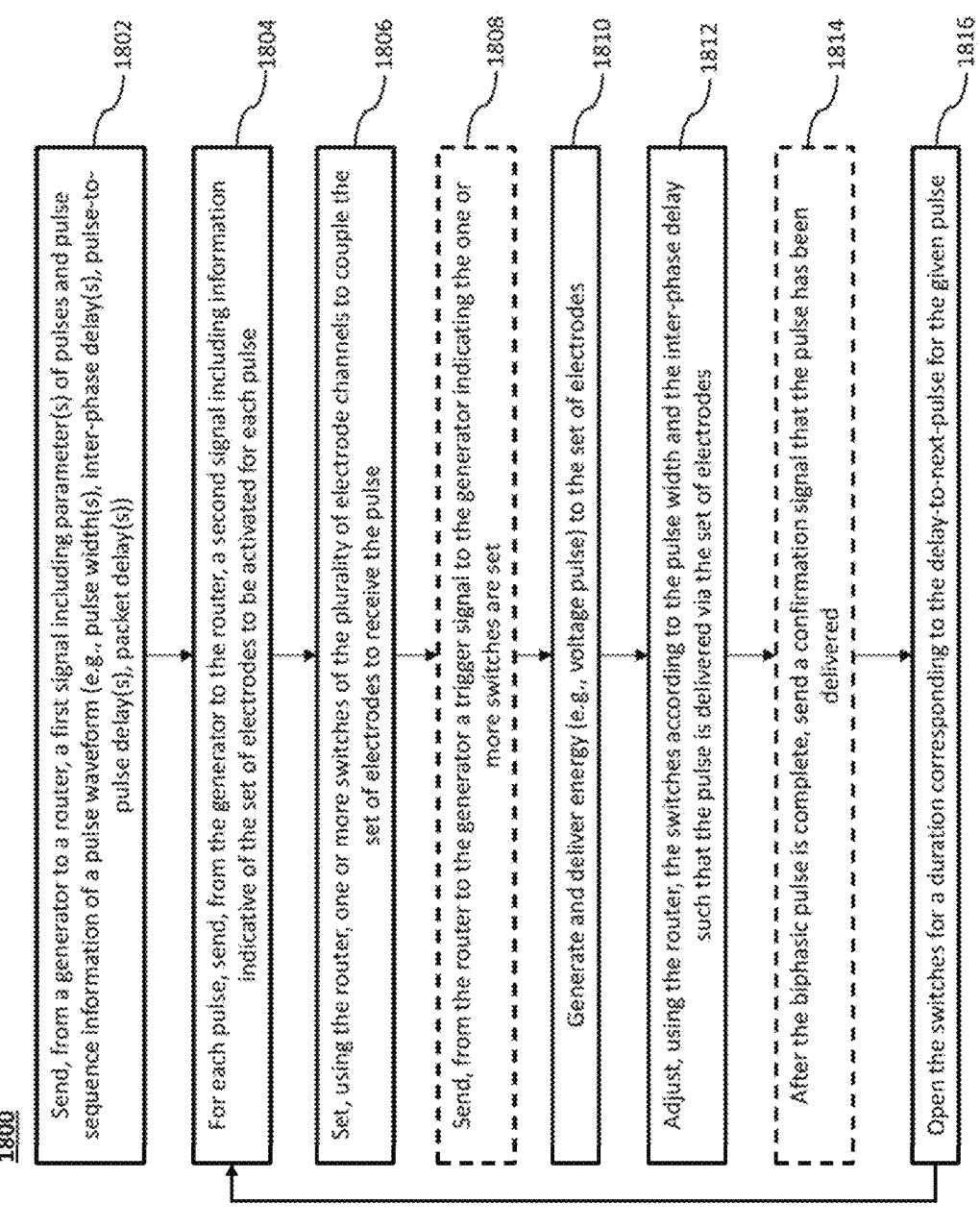

1800

Send, from a generator to a router, a first signal including parameter(s) of pulses and pulse sequence information of a pulse waveform (e.g., pulse width(s), inter-phase delay(s), pulse-to-pulse delay(s), packet delay(s)) — 1802

For each pulse, send, from the generator to the router, a second signal including information indicative of the set of electrodes to be activated for each pulse — 1804

Set, using the router, one or more switches of the plurality of electrode channels to couple the set of electrodes to receive the pulse — 1806

Send, from the router to the generator a trigger signal to the generator indicating the one or more switches are set — 1808

Generate and deliver energy (e.g., voltage pulse) to the set of electrodes — 1810

Adjust, using the router, the switches according to the pulse width and the inter-phase delay such that the pulse is delivered via the set of electrodes — 1812

After the biphasic pulse is complete, send a confirmation signal that the pulse has been delivered — 1814

Open the switches for a duration corresponding to the delay-to-next-pulse for the given pulse — 1816

FIG. 23

APPARATUS, SYSTEMS AND METHODS FOR SOFT TISSUE ABLATION

CROSS-REFERENCE TO RELATED APPLICATIONS

This application is a continuation of U.S. patent application Ser. No. 19/172,274, filed Apr. 7, 2025, now U.S. Pat. No. 12,426,933, titled "APPARATUS, SYSTEMS AND METHODS FOR SOFT TISSUE ABLATION," which is a divisional of U.S. patent application Ser. No. 18/976,095, filed Dec. 10, 2024, now U.S. Pat. No. 12,446,943, titled "APPARATUS, SYSTEMS AND METHODS FOR SOFT TISSUE ABLATION," which is a continuation-in-part of PCT Application No. PCT/US2023/025064, filed Jun. 12, 2023, titled "APPARATUS, SYSTEMS AND METHODS FOR SOFT TISSUE ABLATION," which claims priority to and the benefit of U.S. Provisional Patent Application No. 63/351,197, filed Jun. 10, 2022, titled "APPARATUS, SYSTEMS AND METHODS FOR SOFT TISSUE ABLA- TION," the disclosures of each of which is incorporated by reference in its entirety.

BACKGROUND

Soft tissue ablation is a treatment methodology of relevance to a variety of clinical applications, from cancer therapy delivery for the ablation of several tumor types to the ablation of benign tumors such as fibroids, to the treatment of diseased tissue that could lead to cancer, and to the ablation of sympathetic or parasympathetic nerves in several scenarios. Thermal modalities such as radiofrequency (RF) ablation, cryoablation or ablation with ultrasound have been employed in several applications. These often carry the risk of collateral damage and considerable tissue necrosis in the treated areas.

Pulsed field ablation, also known as irreversible electroporation, has emerged as a potentially useful ablation modality that has been investigated in some tumor applications and has recently been found to be fruitful in the context of cardiac ablation for the treatment of cardiac arrhythmias. This non-thermal ablation modality can be tissue selective and minimize collateral damage while also resulting in a post-ablation natural healing process that preserves the extracellular matrix and overall tissue integrity. While devices and waveforms have been devised that are appropriate in the cardiac ablation context, there is a need for new devices and tools and waveforms that may be more appropriate for use in the context of soft tissue ablation.

The present disclosure addresses the need for systems and waveforms for the efficient and effective delivery of pulsed field ablation therapy, especially for soft tissue ablation. Pulsed field ablation procedures can be rapid while at the same time minimizing collateral tissue damage often seen in thermal-based therapies. At the same time, post-procedural healing can be relatively quick with minimal side-effects.

BRIEF DESCRIPTION

The present disclosure discloses systems and methods for therapy delivery in soft tissue ablation applications. Specifically, the systems, apparatus and methods of this disclosure provide for the generation of high voltage pulsed waveforms delivered to electrodes disposed near tissue for the rapid and efficient ablation of tissue. The electrodes can be disposed on minimally invasive interventional devices that are introduced into a subject anatomy, for example, through endoscopic, laparoscopic, endovascular or percutaneous access and in embodiments can include a reference electrode patch placed on the patient. The devices can be used in a variety of clinical applications. In general, the interventional devices can have a multiplicity of electrodes for therapy delivery. In embodiments, the apparatus for pulse delivery can include a pulse generator for the generation of a pulsed waveform. In embodiments, the apparatus for pulse delivery can also include a high voltage signal router for routing the pulses generated by the pulse generator to an appropriate set of electrodes. In embodiments, the pulse generator and the signal router can be separate pieces of equipment intended for modular connection, while in other embodiments, the pulse generator and signal router can be integrated into a single piece of equipment wherein respective circuit boards all reside. In embodiments, the signal router can incorporate multiple output channels with each channel configured as two half-bridges with a top switch and a bottom switch connected to positive and negative terminals respectively of a voltage source. In a baseline state, all the switches are open and there is no electrical path for current flow. Each output channel of the signal router is intended for connection to an electrode or a set of electrodes. When it is desired to pair two channels as electrode terminals for ablation delivery, the top switch of one channel and the bottom switch of the other channel are closed to create an electrical path and to enable the pairing and voltage and current delivery across the appropriate device electrodes.

In embodiments, the pulsed waveform has specific characteristics as detailed herein. In embodiments, the waveform can comprise at least one pulse train with multiple biphasic, approximately rectangular, pulses with the positive and negative phases (e.g., generally having approximately equal and opposite amplitudes) separated by an inter-phase delay. Thus, each complete biphasic pulse comprises a positive phase, a negative phase, and a delay between the positive and negative phases. In embodiments, the inter-phase delay is larger than the pulse width of the positive or negative phase. In embodiments, the inter-phase delay can be at least about 3 times larger than the pulse width of the positive or negative phase, and in embodiments, it can be at least about 5 times the pulse width of the positive or negative phase. Furthermore, the time delay between one complete biphasic pulse and the next biphasic pulse of the pulse train (referred to as the pulse-to-pulse delay) is not constant across the entire pulse train but rather the sequence of such delays has variations in the delays. For example, in embodiments the sequence of delays follows an increasing pattern for at least one-third of the number of such delays between pulses. In embodiments, the pulse-to-pulse delay sequentially follows a decreasing pattern for at least one-third of the number of such delays between pulses.

In embodiments, the sequence of increasing or decreasing pulse-to-pulse delays follows at least an arithmetical progression, e.g., the magnitude of the difference between one pulse-to-pulse delay and its immediate predecessor is at least a non-zero constant. In embodiments, the sequence of increasing or decreasing pulse-to-pulse delays follows at least a geometric progression, e.g., the ratio of one pulse-to-pulse delay to its immediate predecessor is at least a constant greater than 1 in the case of a sequence of increasing delays, or it is smaller than or equal to a constant less than 1 in the case of a sequence of decreasing delays. In embodiments, the ratio of one pulse-to-pulse delay to its immediate predecessor in an increasing sequence of delays is at least about 1.1. In embodiments, the ratio of one pulse-to-pulse delay to its immediate predecessor in a decreasing sequence of delays is less than about 0.9.

In embodiments, in a given pulse train, the pulse-to-pulse delay sequentially follows an increasing pattern for at least one-third of the number of such delays between pulses and follows a decreasing pattern for at least one-third of the number of such delays between pulses. In embodiments, the entire waveform comprises a multiplicity of such pulse trains (each of which is also referred to as a packet of pulses), with successive pulse packets separated by a packet delay. In embodiments, the packet delay is not constant but can vary over the packets.

In embodiments, in each pulse of the pulse train, each phase (positive or negative) is trapezoidal or substantially trapezoidal in shape. In this case, the pulse width is defined as the width of one phase of the pulse where the voltage has a value greater than about 70% of the amplitude of the pulse. A complete biphasic pulse comprises a positive phase, a negative phase, and an inter-phase delay between the positive and negative phases. In embodiments, the inter-phase delay is larger than the width of the positive or negative phase. In embodiments, the inter-phase delay can be at least about 3 times larger than the width of the positive or negative phase, and in embodiments, it can be at least about 5 times the width of the positive or negative phase. Furthermore, the time delay between one complete biphasic pulse and the next biphasic pulse of the pulse train, or pulse-to-pulse delay, is not constant across the pulse train but rather the sequence of such delays follows an increasing pattern for at least one-third of the number of such delays between pulses. In embodiments, the pulse-to-pulse delay sequentially follows a decreasing pattern for at least one-third of the number of such delays between pulses. In embodiments, in a given pulse train, the pulse-to-pulse delay sequentially follows an increasing pattern for at least one-third of the number of such delays between pulses and follows a decreasing pattern for at least one-third of the number of such delays between pulses. In embodiments, the entire waveform comprises a multiplicity of such pulse trains or packets, with successive pulse packets separated by a packet delay. In embodiments, the packet delay is not constant but can vary over the packets.

In some embodiments, waveform delivery can be sequenced over a set of electrode pairings. In embodiments, if the waveform comprises a set of pulse packets, the pulse packets can be all delivered first to one electrode pair, followed by delivery of all pulse packets to a second electrode pair, and so on. In other embodiments, the pulse packets as defined here can be interleaved over electrode pairs. In this case, a first pulse packet can be delivered to a first electrode pair, and during the packet delay time interval, a first pulse packet can be delivered to a second electrode pair, and so on. Then a second pulse packet can be delivered to the first electrode pair, followed by delivery of a second pulse packet to a second electrode pair, and so on, all during the next packet delay. This process can continue until the complete waveform has been delivered to all electrode pairs.

In still other embodiments, a single packet or pulse train can interleave pulses applied to different electrode pairings. In this case, a first pulse of the pulse train is applied to a first electrode pair, and during the pulse-to-pulse delay before the next pulse applied to the first electrode pair, a first pulse can be delivered to a second electrode pair, and so on. Then a second pulse can be delivered to the first electrode pair, followed by delivery of a second pulse to a second electrode pair, and so on, all during the next pulse-to-pulse delay. This process can continue until the complete pulse train has been delivered to all electrode pairs, and the process can be repeated for each of the remaining pulse packets.

In embodiments, the signal router can accomplish the task of managing the timing of various pulse deliveries to appropriate electrode pairs and/or managing the interleaving process. The logic for this can be implemented in electronic form, for example, on a microcontroller or other type of processing device. In general, the generator system can comprise the pulse generator and the signal router. In embodiments, once a specific device is connected to the generator system, the system can automatically detect the device and determine the specific waveform and sequencing scheme appropriate to that device from a pre-determined list of options. In embodiments, the generator system can comprise only a signal generator (or pulse generator) and no signal router, as can be the case when the interventional device and ablation delivery requires only a single pair of electrodes or electrode sets. In any of the embodiments described in this disclosure, the term "electrode" can refer to an electrode directly on an interventional device or to a surface electrode patch or reference electrode placed on the patient.

The devices used for ablation delivery with the generator system of the present disclosure can be attached or connected to an electrical conductor that attaches to a cable or connector cable for delivery of electrical energy from the generator system for delivery of the high voltage pulsed field ablation waveforms described herein. Generally, such energy delivery is performed in either unipolar or bipolar mode. In unipolar mode, a subset of the electrodes has one electrical polarity, while a reference patch placed on the subject has the opposite electrical polarity. In bipolar mode, two different subsets of electrodes are energized with opposite electrical polarities. In embodiments, multiple paired subsets of electrodes can be energized in sequential fashion for energy delivery. When the pulsed field ablation waveform is applied, the spatial distribution of the resulting electric field determines the zone of cell death. Depending on the value of the irreversible electroporation threshold for a given targeted cell type, cells in a spatial zone where the electric field magnitude is greater than the threshold value are killed or ablated, while cells in other spatial zones where the electric field magnitude is below the threshold value survive. In embodiments, the ablation can generate an electric field not sufficient to cause irreversible electroporation but sufficient to cause reversible electroporation, wherein cell membranes in the zone of reversible electroporation are permeabilized to permit the passage of drug molecules or other therapeutic agents into the cells, for example, to treat cancer.

In embodiments, the voltage amplitude of the waveforms described herein can range from approximately 300 V to approximately 10,000V depending on the application, including all values and ranges therebetween. The pulse widths of the waveform can range from approximately 0.5 microseconds to approximately 150 microseconds, including all values and ranges therebetween. The inter-phase delay can range from approximately 5 microseconds to approximately 3 milliseconds, including all values and ranges therebetween. The pulse-to-pulse delay can range from approximately 15 microseconds to approximately 500 milliseconds, including all values and ranges therebetween, and the packet delay can range from 300 milliseconds to approximately 12 seconds, including all values and ranges therebetween.

In some embodiments, an apparatus includes: a pulse generator configured to be coupled to an ablation device, the pulse generator configured to generate a voltage pulse train including a plurality of biphasic pulses, each biphasic pulse of the plurality of biphasic pulses including a positive pulse, a negative pulse, and an inter-phase delay separating the positive pulse and the negative pulse, successive biphasic pulses of the plurality of biphasic pulses being separating by a pulse-to-pulse delay such that the plurality of biphasic pulses is separated by a plurality of pulse-to-pulse delays, and the plurality of pulse-to-pulse delays including an increasing sequence of pulse-to-pulse delays including a subset of successive pulse-to-pulse delays that progressively increase.

In some embodiments, an apparatus includes: a pulse generator configured to be coupled to an ablation device, the pulse generator configured to generate a voltage pulse train including a plurality of biphasic pulses, each biphasic pulse of the plurality of biphasic pulses including a positive pulse, a negative pulse, and an inter-phase delay separating the positive pulse and the negative pulse, successive biphasic pulses of the plurality of biphasic pulses being separating by a pulse-to-pulse delay such that the plurality of biphasic pulses is separated by a plurality of pulse-to-pulse delays, and the plurality of pulse-to-pulse delays including a decreasing sequence of pulse-to-pulse delays including a subset of successive pulse-to-pulse delays that progressively decrease.

In some embodiments, an apparatus includes: a pulse generator configured to be coupled to an ablation device, the pulse generator configured to generate a voltage pulse train including a plurality of biphasic pulses, each biphasic pulse of the plurality of biphasic pulses including a positive pulse, a negative pulse, and an inter-phase delay separating the positive pulse and the negative pulse, successive biphasic pulses of the plurality of biphasic pulses being separating by a pulse-to-pulse delay such that the plurality of biphasic pulses is separated by a plurality of pulse-to-pulse delays, and the plurality of pulse-to-pulse delays including: an increasing sequence of pulse-to-pulse delays including a first subset of successive pulse-to-pulse delays that progressively increase; and a decreasing sequence of pulse-to-pulse delays including a second subset of successive pulse-to-pulse delays that progressively decrease.

In some embodiments, a system includes: a pulse generator configured to generate biphasic pulses each including a positive pulse, a negative pulse, and an inter-phase delay; a signal router operatively coupled to the pulse generator and a plurality of electrode sets each including one or more electrodes, the signal router configured to: (1) set one or more switches to selectively apply the biphasic pulses generated by the pulse generator to one or more electrode sets of the plurality of electrode sets and (2) generate a series of trigger signals to trigger the pulse generator to generate the biphasic pulses; and a communication channel disposed between the signal router and the pulse generator, the communication channel configured to transmit the series of trigger signals to the pulse generator such that the pulse generator, in response to receiving each trigger signal of the series of trigger signals, generates a pulse train and delivers the pulse train to the signal router to be applied to one or more electrode sets of the plurality of electrode sets, the pulse train including a plurality of biphasic pulses with successive biphasic pulses of the plurality of biphasic pulses being separated by a pulse-to-pulse delay of a plurality of pulse-to-pulse delays, the plurality of pulse-to-pulse delays including at least one of: an increasing sequence of pulse-to-pulse delays including a subset of successive pulse-to-pulse delays that progressive increase; or a decreasing sequence of pulse-to-pulse delays including a subset of successive pulse-to-pulse delays that progressive decrease.

In some embodiments, a method includes: generating, using a pulse generator coupled to an ablation device, a voltage pulse train including a plurality of biphasic pulses, each biphasic pulse of the plurality of biphasic pulses including a positive pulse, a negative pulse, and an inter-phase delay separating the positive pulse and the negative pulse, successive biphasic pulses of the plurality of biphasic pulses being separating by a pulse-to-pulse delay such that the plurality of biphasic pulses is separated by a plurality of pulse-to-pulse delays, and the plurality of pulse-to-pulse delays including an increasing sequence of pulse-to-pulse delays including a subset of successive pulse-to-pulse delays that progressively increase.

In some embodiments, a method includes: generating, using a pulse generator coupled to an ablation device, a voltage pulse train including a plurality of biphasic pulses, each biphasic pulse of the plurality of biphasic pulses including a positive pulse, a negative pulse, and an inter-phase delay separating the positive pulse and the negative pulse, successive biphasic pulses of the plurality of biphasic pulses being separating by a pulse-to-pulse delay such that the plurality of biphasic pulses is separated by a plurality of pulse-to-pulse delays, and the plurality of pulse-to-pulse delays including a decreasing sequence of pulse-to-pulse delays including a subset of successive pulse-to-pulse delays that progressively decrease.

In some embodiments, a method includes: generating, using a pulse generator coupled to an ablation device, a voltage pulse train including a plurality of biphasic pulses, each biphasic pulse of the plurality of biphasic pulses including a positive pulse, a negative pulse, and an inter-phase delay separating the positive pulse and the negative pulse, successive biphasic pulses of the plurality of biphasic pulses being separating by a pulse-to-pulse delay such that the plurality of biphasic pulses is separated by a plurality of pulse-to-pulse delays, and the plurality of pulse-to-pulse delays including: an increasing sequence of pulse-to-pulse delays including a subset of successive pulse-to-pulse delays that progressively increase; and a decreasing sequence of pulse-to-pulse delays including a subset of successive pulse-to-pulse delays that progressively decrease.

7

Figure 7:
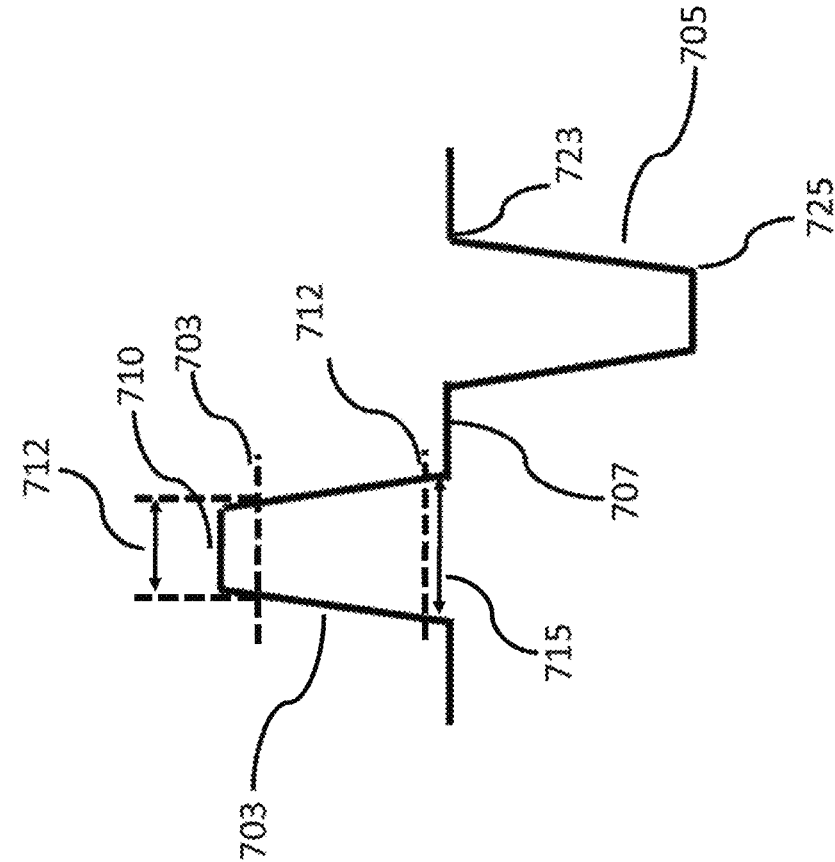

FIG. 7 illustrates a trapezoidal biphasic pulse with pulse width and pulse base elements identified, according to embodiments.

Figure 8:
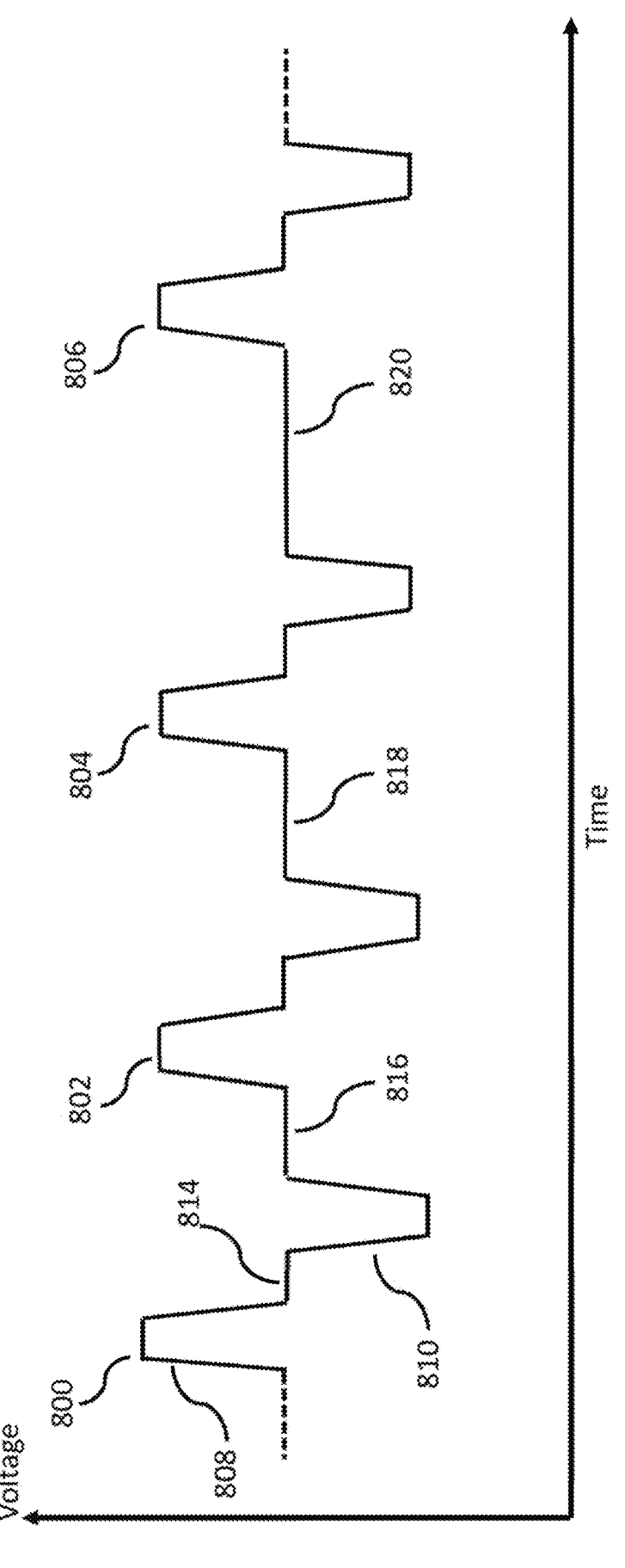

FIG. 8 illustrates an embodiment of a trapezoidal pulse train of the present disclosure with an increasing sequence of pulse-to-pulse delays.

Figure 9:
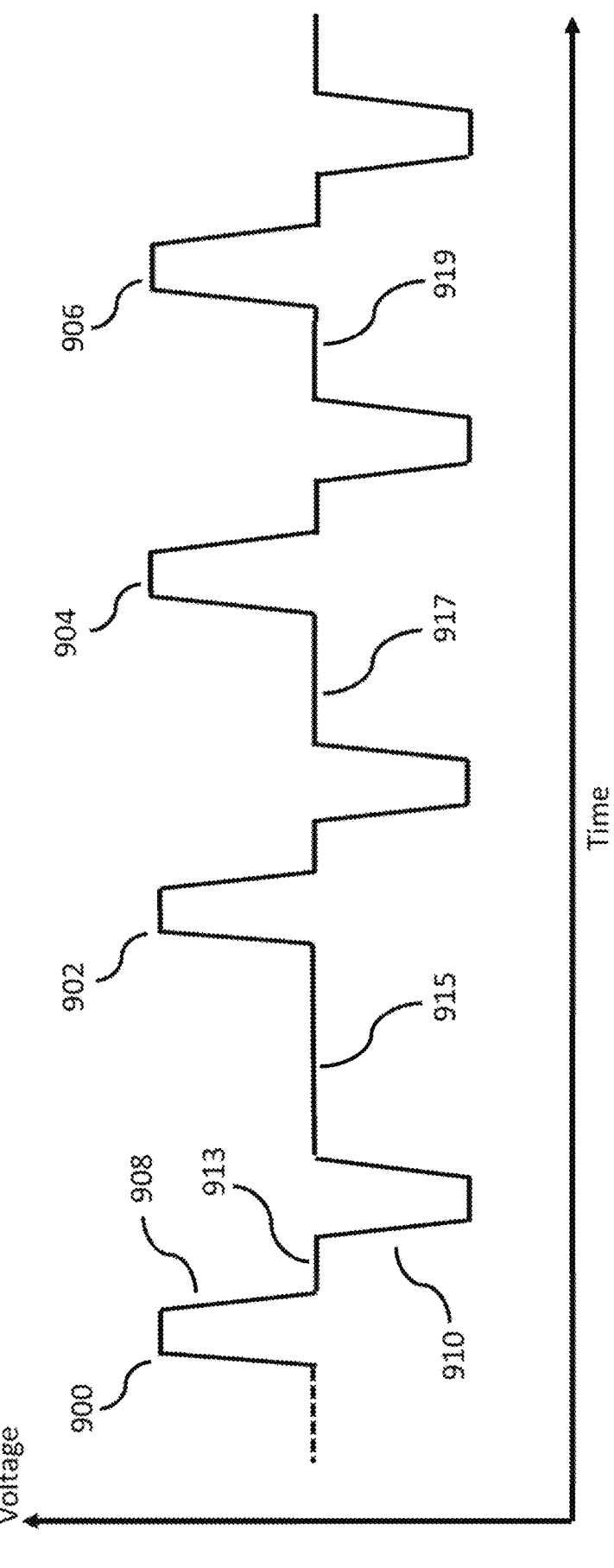

FIG. 9 illustrates a trapezoidal pulse train of the present disclosure with a decreasing sequence of pulse-to-pulse delays.

Figure 10:
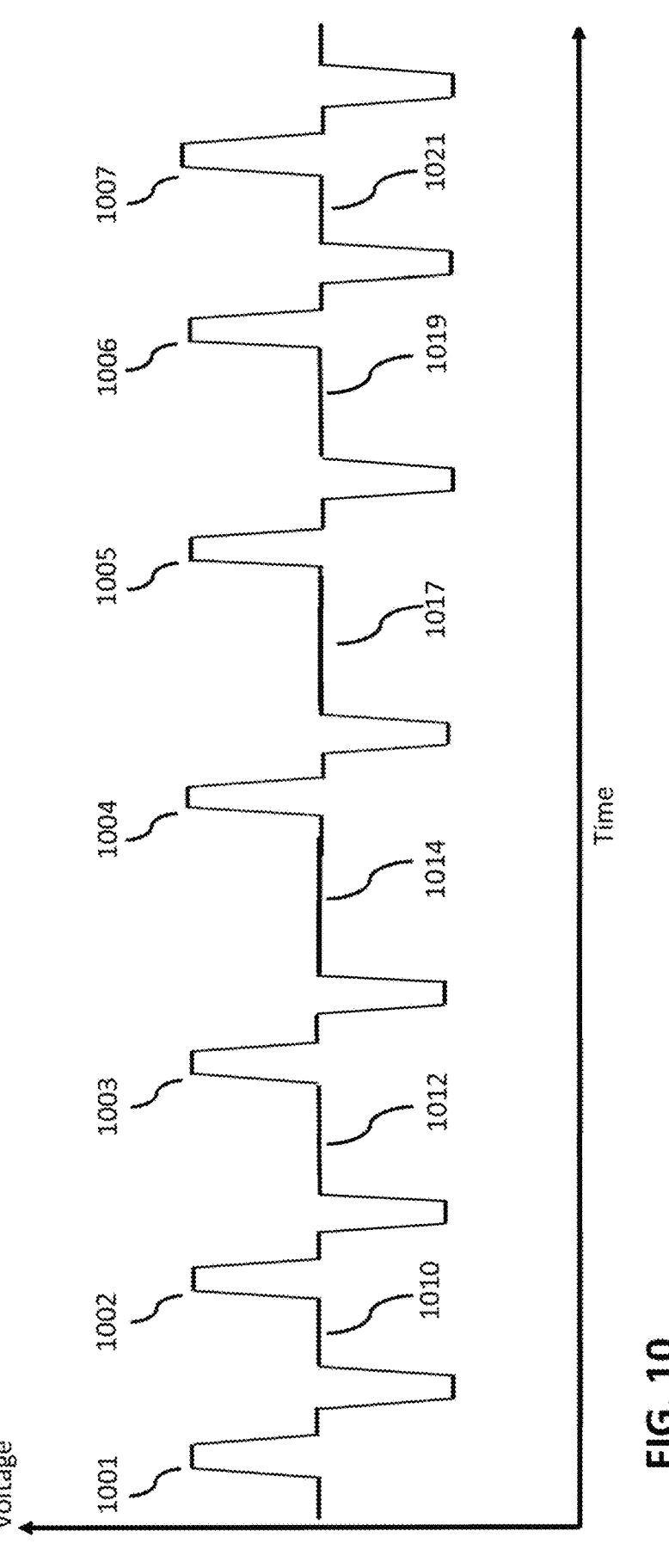

FIG. 10 illustrates an embodiment of a trapezoidal pulse train of the present disclosure having both an increasing sequence of pulse-to-pulse delays and a decreasing sequence of pulse-to-pulse delays.

Figure 11:
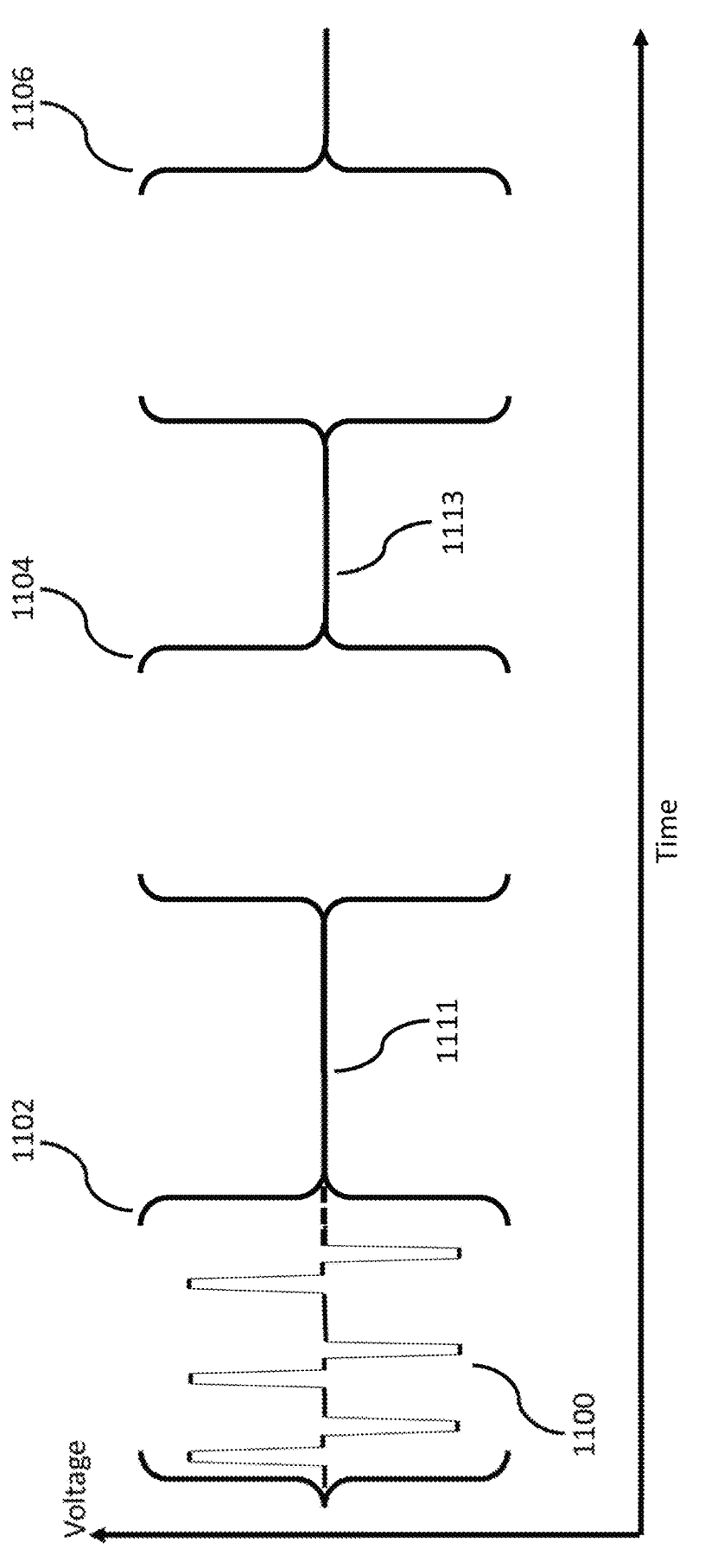

FIG. 11 illustrates a waveform with multiple packets of pulse trains with packet delays across the series of packets, according to embodiments.

Figure 12:
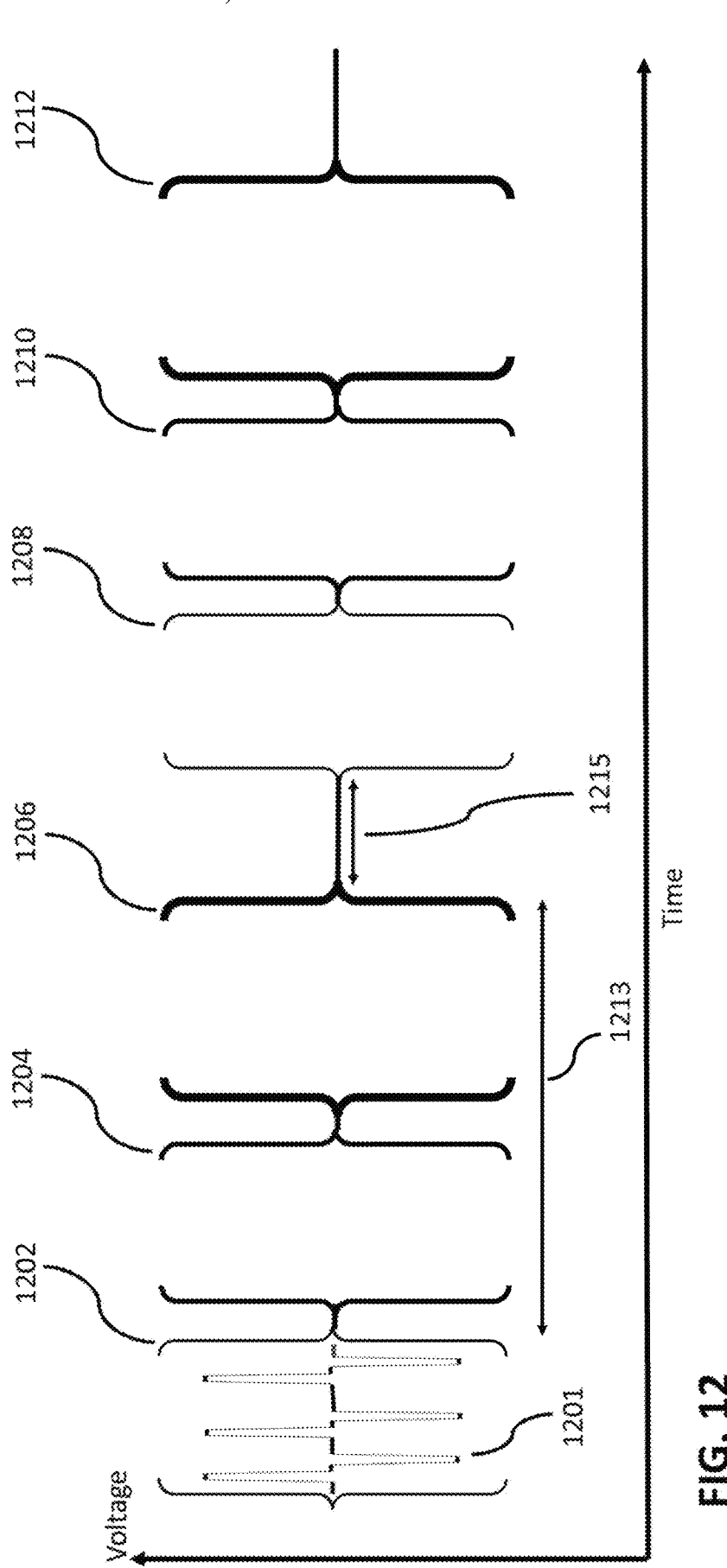

FIG. 12 illustrates sequenced delivery of a waveform in the form of a multiplicity of pulse packets delivered to a multiplicity of electrode pairs, according to embodiments.

Figure 13:
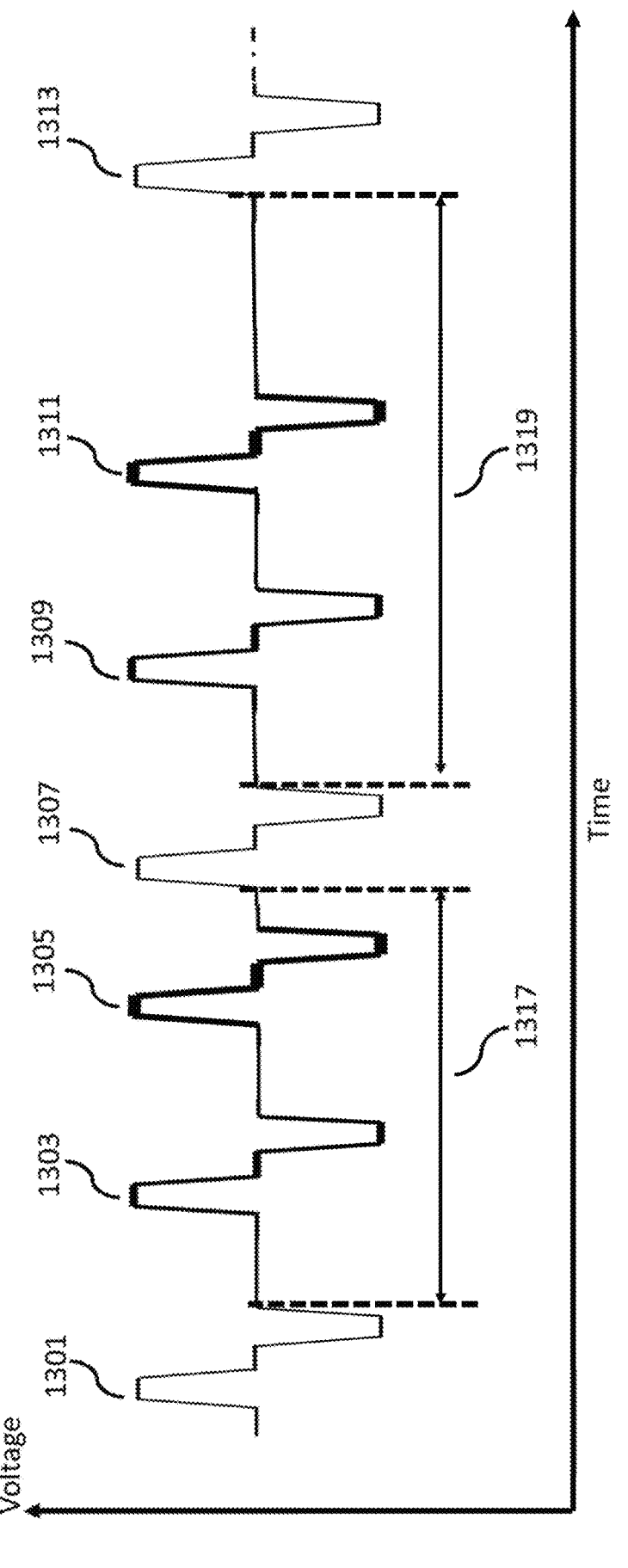

FIG. 13 illustrates sequenced delivery of a pulse train of a waveform in the form of individual pulses of a pulse train respectively delivered to a multiplicity of electrode pairs in interleaved fashion, according to embodiments.

Figure 14:
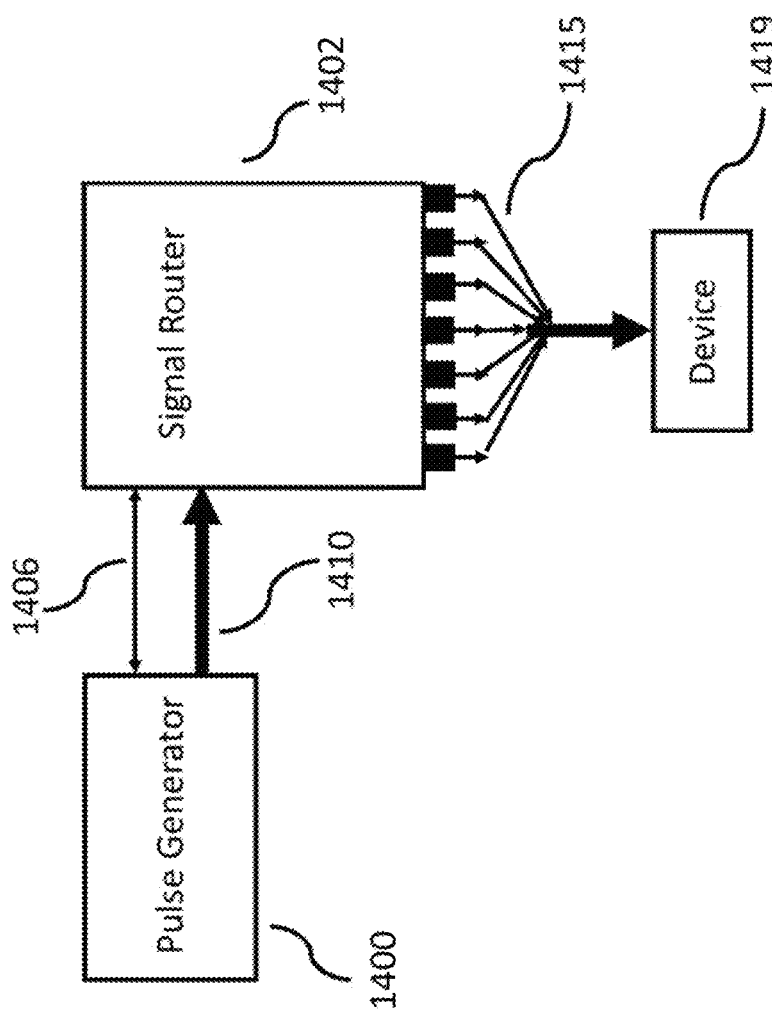

FIG. 14 is a schematic illustration of a generator system in the form of a pulse generator and a signal router for delivery of a pulsed field ablation waveform to a medical device, according to embodiments.

Figure 15:
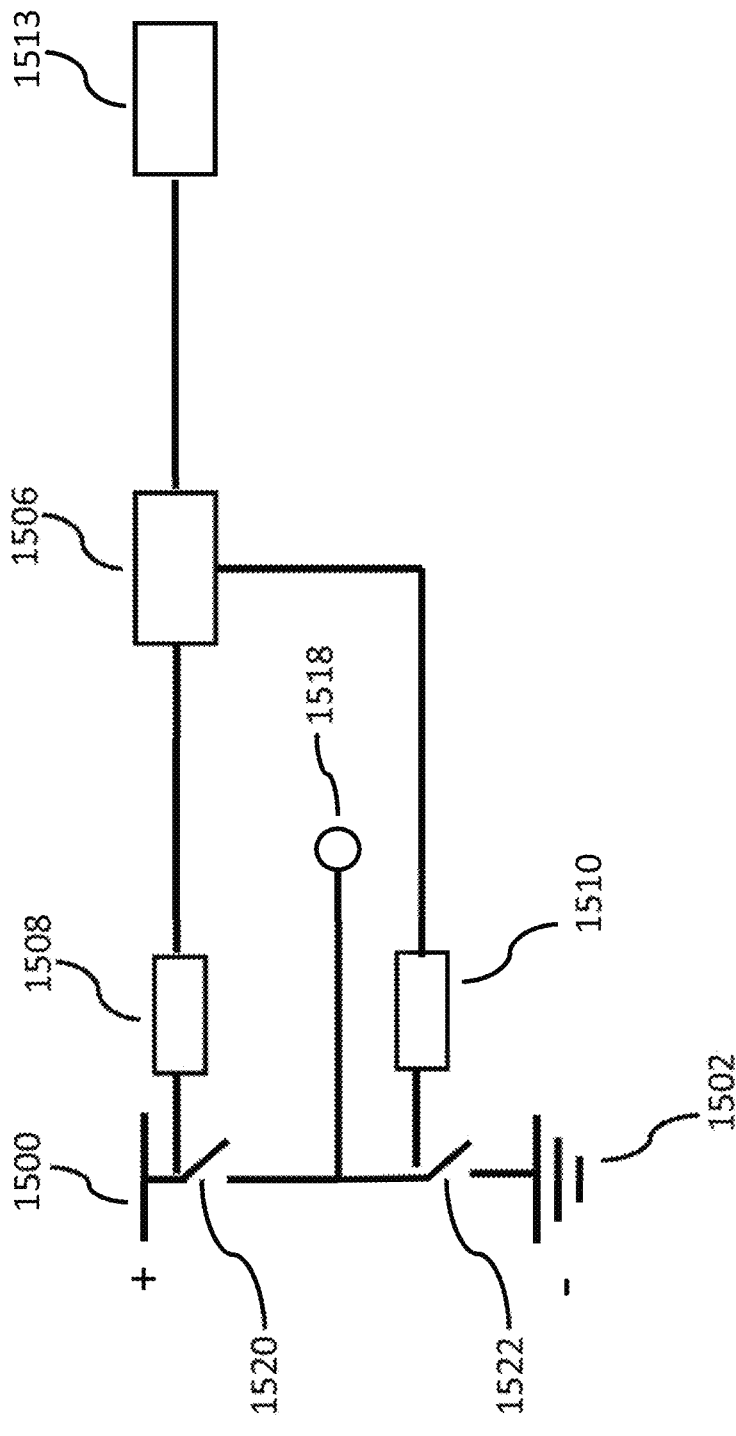

FIG. 15 is a schematic illustration of control circuitry for operation of a single channel of a generator system, according to embodiments of the present disclosure.

Figure 16:
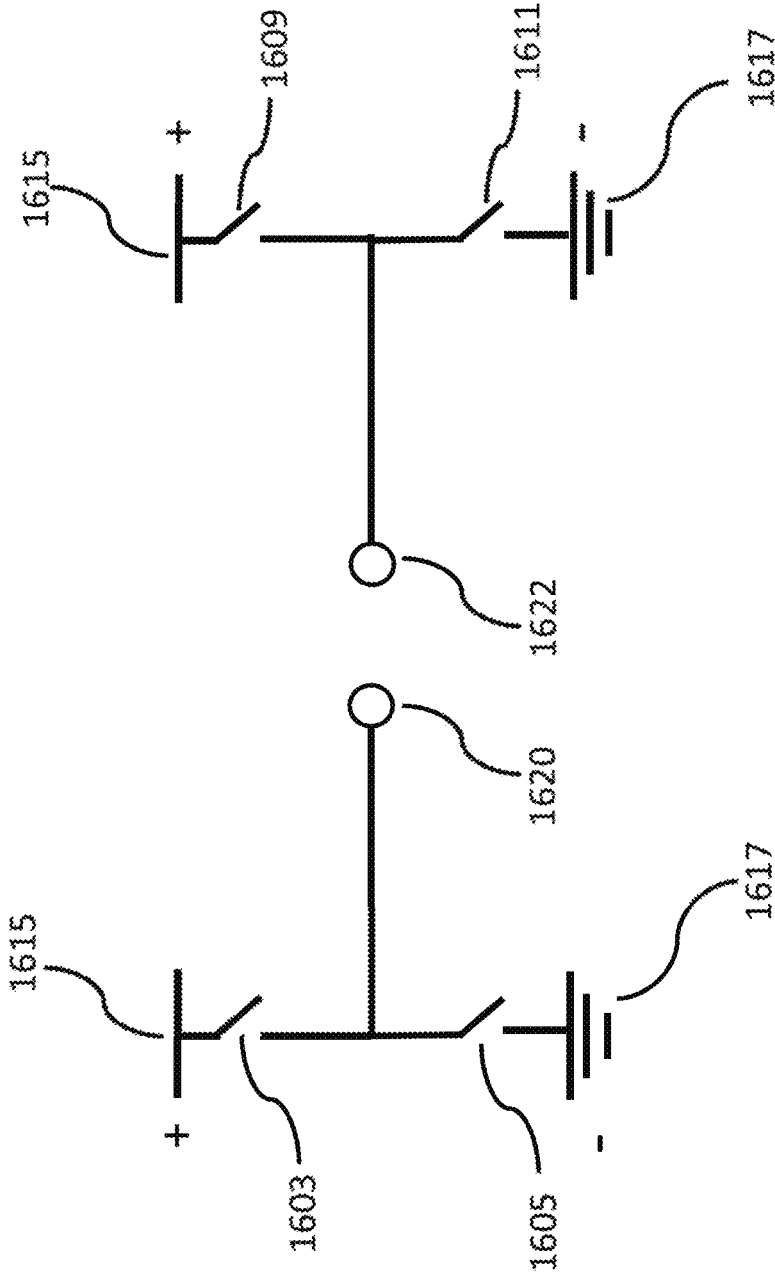

FIG. 16 illustrates the half bridge topology of two channels of a generator system that can be combined to deliver a pulsed field ablation waveform to a pair of electrodes respectively connected to the two channels, according to embodiments.

Figure 17:
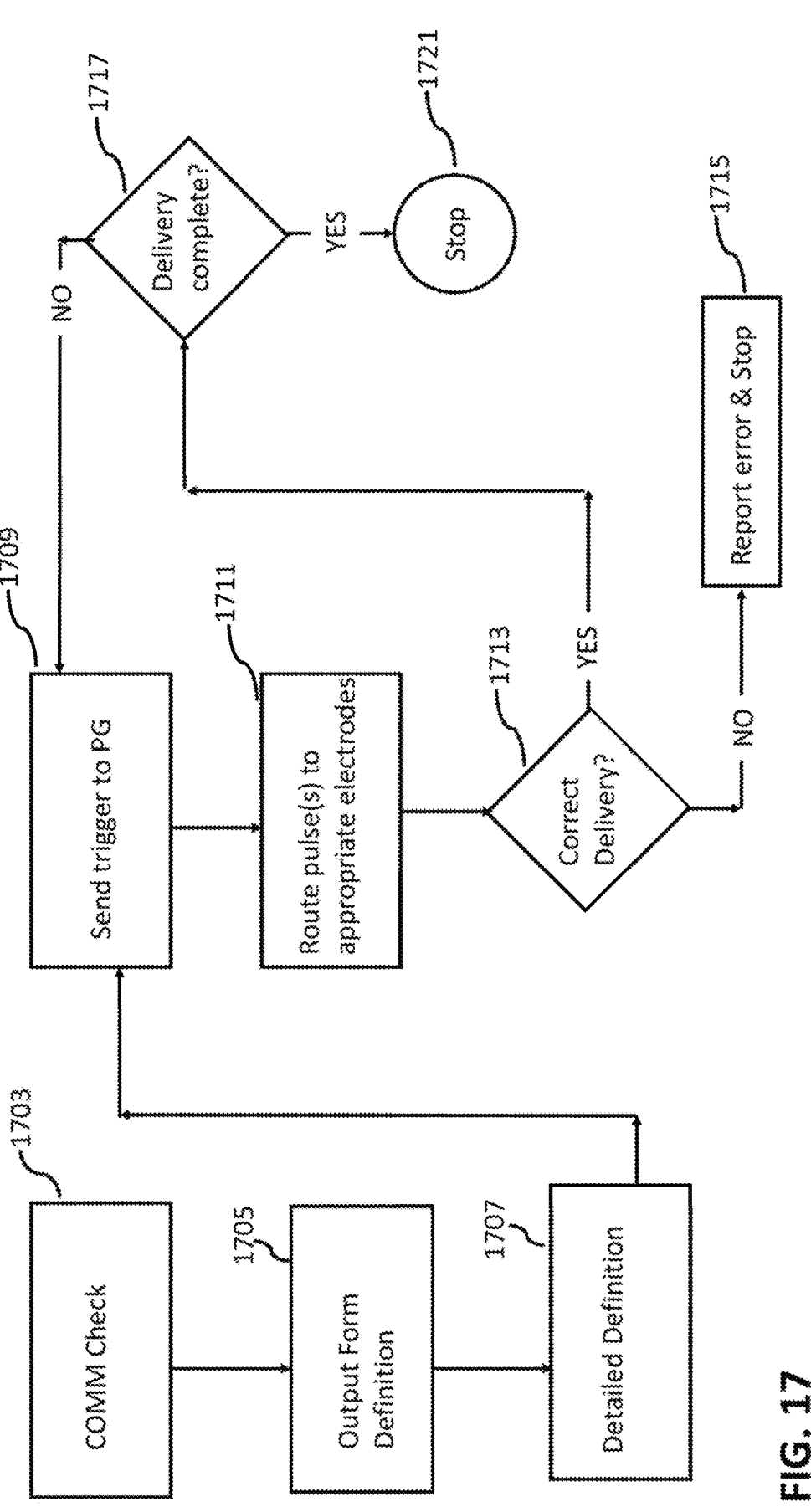

FIG. 17 illustrates the operation of the system of the present disclosure in an embodiment.

FIGS. 18-21 show example pulse waveform tables including pulse parameters a pulse generator is configured to send to the signal router, according to embodiments.

Figure 22:
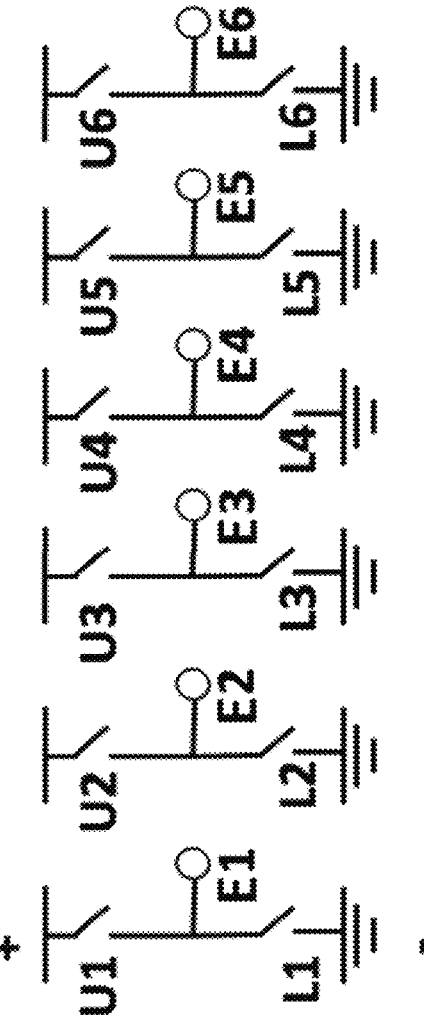

FIG. 22 is a schematic illustration of control circuitry for operation of electrode channels for delivering biphasic pulses to electrodes, according to embodiments.

FIG. 23 is a flow chart of an example method of implementing a pulse waveform sequence using a generator and control circuitry that is operatively coupled to a plurality of electrodes, according to an embodiment.

DETAILED DESCRIPTION

The embodiments of the present disclosure generally provide for delivering customized waveforms disclosed herein for the pulsed field ablation of soft tissue structures, e.g., for cancer therapy delivery for the ablation of several tumor types, for the ablation of benign tumors such as fibroids, for the treatment of diseased tissue that could lead to cancer, or the ablation of sympathetic or parasympathetic nerves, among others.

Figure 1:
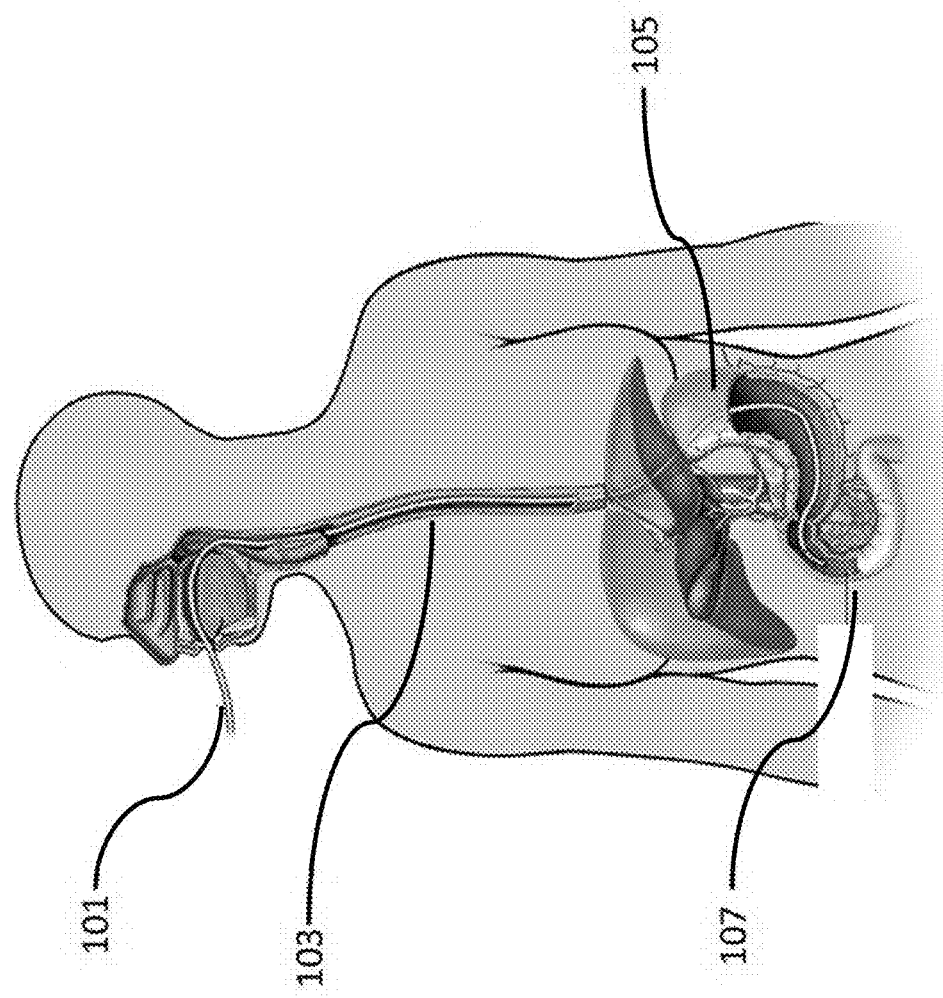
FIG. 1 is a schematic illustration of an endoscope passing through the stomach of a subject and placed in the duodenum.

As an example, for the treatment of pancreatic tumors, endoscopic access can be gained to the stomach or the duodenum, and an adjacent organ such as the pancreas can be subsequently accessed by suitable puncture. FIG. 1 shows an endoscope 101 inserted through a subject's mouth and down the esophagus 103 to be positioned at the duodenum 107 after passing through the stomach 105. This type of positioning can place the endoscope near the pancreas.

8

Figure 2:
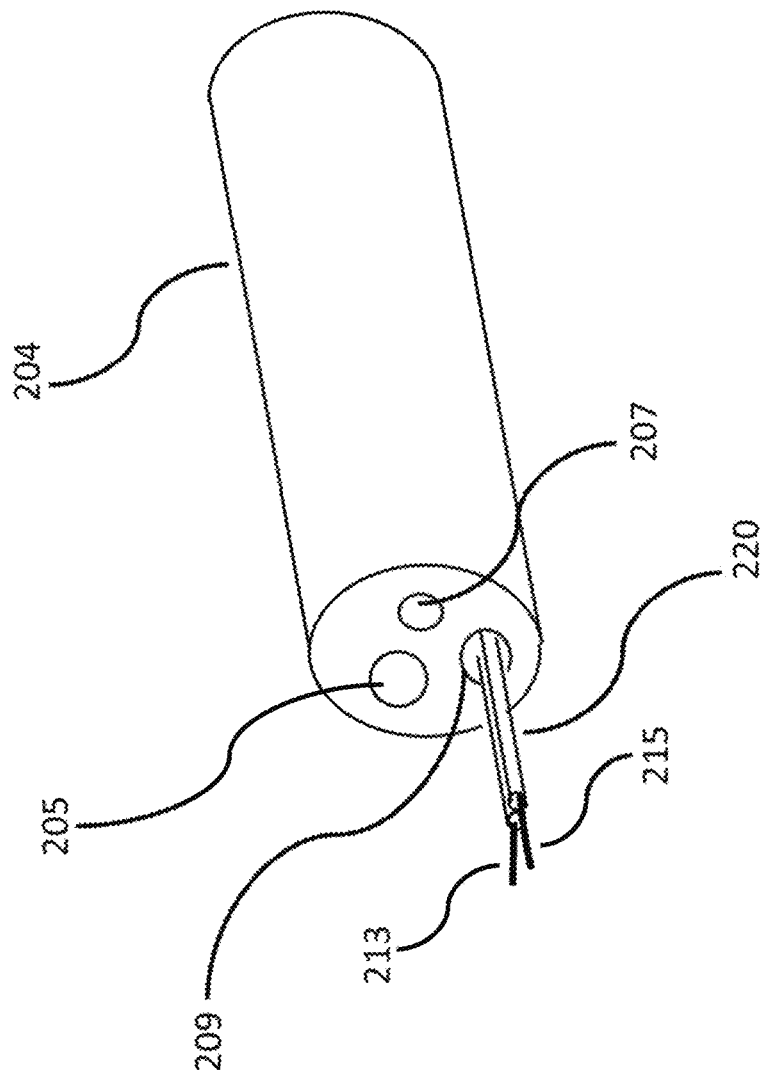
FIG. 2 is a schematic illustration of the distal portion of an endoscope with multiple lumens, with one of the lumens being used for the passage of a catheter device with electrodes for ablation delivery, according to embodiments.

FIG. 2 shows, for illustrative and example purposes, the distal portion of an endoscope 204 with multiple lumens 205, 207 and 209. The lumens 205 and/or 207 can be used for passage of an optical imaging fiber or camera or an ultrasound imaging catheter. The lumen or channel 209 is shown as being used for the passage of a catheter device 220 that itself has two lumens carrying the needles or needle wires 213 and 215. The endoscope can be steered to an appropriate location in the stomach or the duodenum that helps with the proper deployment and placement of the needles 213 and 215. In use, the endoscope 204 is passed through the mouth and esophagus to the stomach and/or duodenum and placed adjacent to or near a tissue wall, for example, close to the pancreas. The catheter 220 is extended under image guidance from optical or ultrasound imaging carried out with the appropriate imaging device used with the endoscope, and is positioned at an appropriate location for access to a suitable pancreatic site. The needles 213 and 215 are extended out of the catheter device 220 and used to puncture the stomach wall and enter the pancreas to access a target tumor site. Once the needles 213 and 215 are positioned suitably in the pancreas, pulsed field ablation is delivered through the needles from the generator system (described below) that is connected to the catheter 220.

Figure 3:
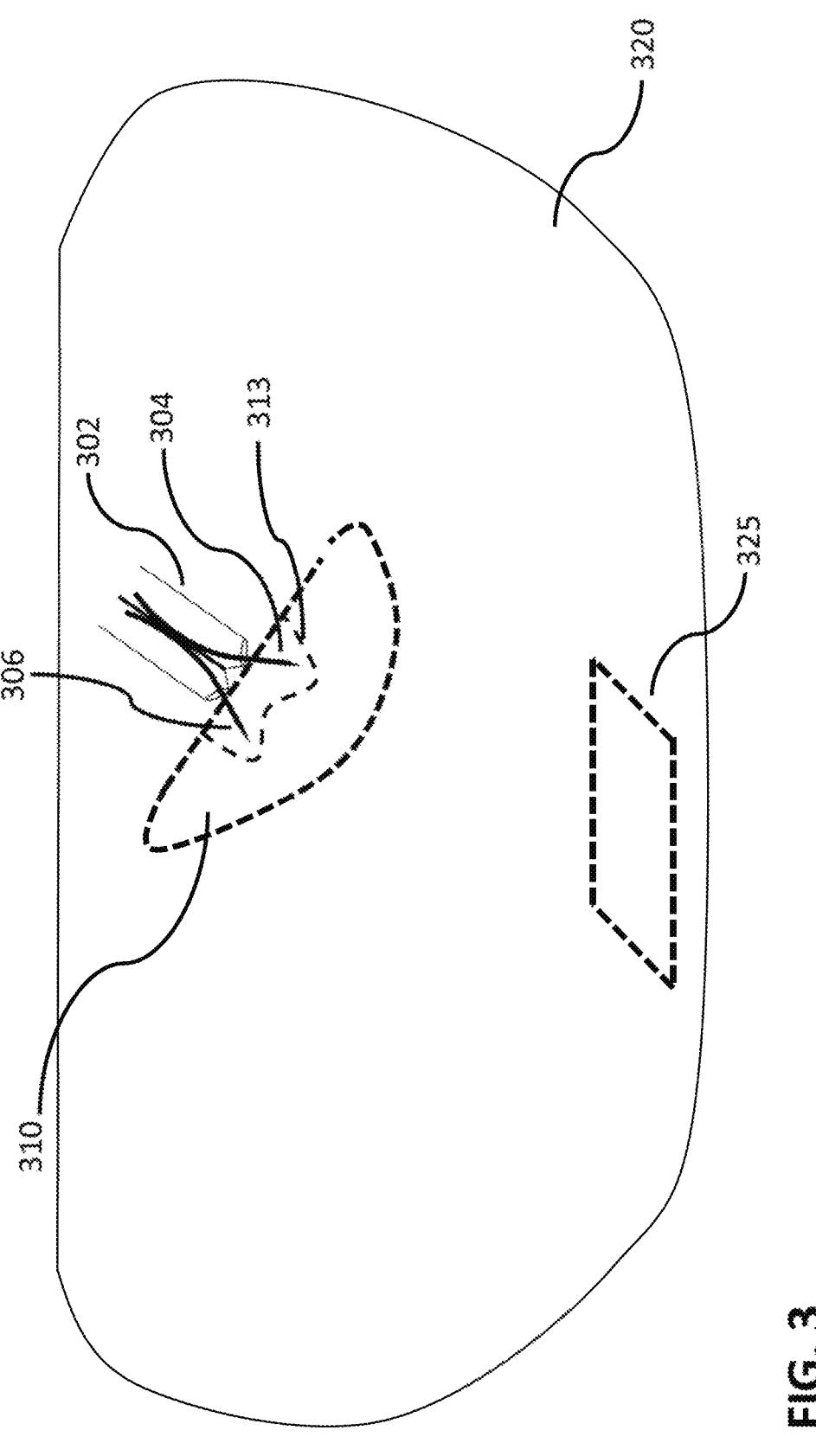
FIG. 3 is an illustration of a catheter device with needle electrodes placed in an organ within a subject, with the figure also showing a reference patch, according to embodiments.

FIG. 3 is an illustration of a catheter device 302 that is placed adjacent to anatomical organ 310 within a subject body 320 (shown in the figure in cross section), according to embodiments. Needles 304 and 306 are extended from the device lumens to penetrate and enter organ 310. In one embodiment, the needles can be used as a single, joint electrode (i.e., polarized with one electrical polarity) and paired electrically with a reference electrode patch 325 (polarized with the opposite electrical polarity) to deliver pulsed field ablation in unipolar (also called monopolar) mode. In other embodiments, the needles 304 and 306 can be used as a bipolar electrode pair for bipolar pulsed field ablation delivery. Application of a pulsed field ablation waveform to the electrodes results in the generation of an electric field and, depending on the tissue irreversible electroporation threshold, a lesion zone such as the zone with boundary 313 is generated as a result of ablation. If a larger treatment volume or region is desired, the needles 304 and 306 can be retracted, the catheter 302 moved to and positioned at a different location, the needles 304 and 306 inserted at the new location and therapy delivered at the new location.

Systems, devices, and methods described herein can be configured to deliver pulse waveforms, as described below.

Pulse Waveform

Figure 4:
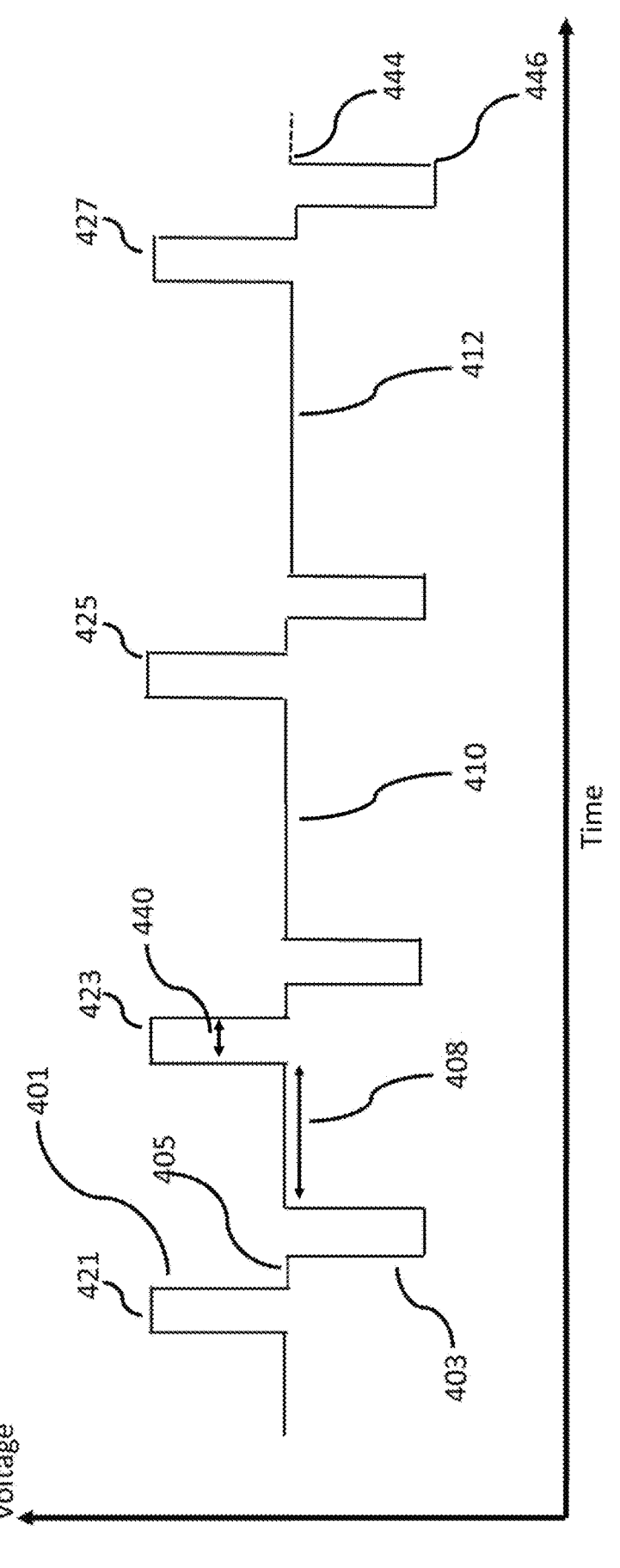
FIG. 4 illustrates an embodiment of a pulse train of the present disclosure with an increasing sequence of pulse-to-pulse delays.

FIGS. 4-13 depict various examples of pulse waveforms, which can be delivered by a device including one or more sets of electrodes, according to embodiments. FIG. 4 illustrates an embodiment of a pulse train of the present disclosure with an increasing sequence of pulse-to-pulse delays. The figure shows a biphasic voltage pulse train as a time sequence with four pulses 421, 423, 425 and 427. Each complete biphasic pulse, such as for example 421, has a positive phase (indicated by 401) and a negative phase (indicated by 403), separated by an inter-phase time delay (indicated by 405). The pulse train shown has pulses with each phase substantially rectangular in form. The pulse width (indicated by 440 in the figure) is the effective duration of each phase. In embodiments, the inter-phase delay can be larger than the width of the positive or negative phase. In embodiments, the inter-phase delay can be at least about 3 times larger than the width of the positive or negative phase, and in embodiments it can be at least about 5 times the width of the positive or negative phase. In embodiments, the corners of the pulses (such as those indicated by 444 and 446 in the figure) can have a rounded shape (not shown). There are time delay intervals, referred to as pulse-to-pulse delays, between successive biphasic pulses. As depicted in FIG. 4, pulse-to-pulse delay 408 (measured from the end of pulse 421 to the start of pulse 423) separates the first pulse 421 and the second pulse 423, pulse-to-pulse delay 410 separates pulse 423 and 425, and pulse-to-pulse delay 412 separates pulse 425 and 427. The pulse-to-pulse delays in general vary over the pulse train and, in at least portions of the pulse train, follow an increasing or decreasing pattern. The schematic illustration in FIG. 4 shows an increasing sequence of pulse-to-pulse delays over time; thus, pulse-to-pulse delay 412 is larger than pulse-to-pulse delay 410, and pulse-to-pulse delay 410 is larger than pulse-to-pulse delay 408.

In embodiments, the sequence of increasing pulse-to-pulse delays follows at least an arithmetical progression, e.g., the difference between one pulse-to-pulse delay and its immediate predecessor is at least a non-zero constant. In embodiments, the sequence of increasing delays follows at least a geometric progression, e.g., the ratio of one pulse-to-pulse delay to its immediate predecessor pulse-to-pulse delay is at least a constant greater than 1. In embodiments, the difference between one pulse-to-pulse delay and its immediate predecessor in an increasing sequence of pulse-to-pulse delays is at least about 10 microseconds, while in other embodiments it is at least about 100 microseconds. In embodiments, the ratio of one pulse-to-pulse delay to its immediate predecessor pulse-to-pulse delay in an increasing sequence of pulse-to-pulse delays is at least about 1.1. In embodiments, the pulse-to-pulse delay sequentially follows an increasing pattern for at least one-third of the total number of such delays between adjacent pulses in the pulse train.

Figure 5:
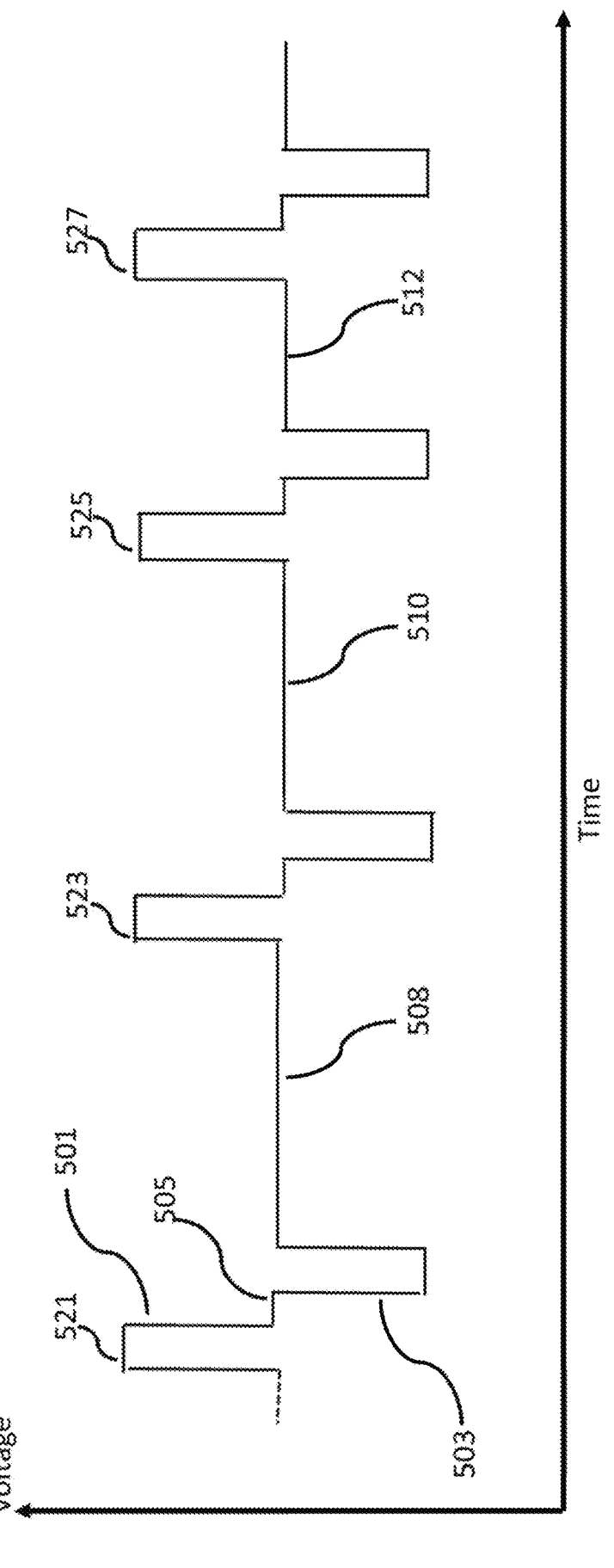
FIG. 5 illustrates an embodiment of a pulse train of the present disclosure with a decreasing sequence of pulse-to-pulse delays.

FIG. 5 illustrates an embodiment of a pulse train of the present disclosure with a decreasing sequence of pulse-to-pulse delays. The FIG. shows a biphasic voltage pulse train as a time sequence with four pulses 521, 523, 525 and 527. Each complete biphasic pulse, such as for example 521, has a positive phase (indicated by 501) and a negative phase (indicated by 503), separated by an inter-phase time delay (indicated by 505). The pulse train shown has pulses with each phase substantially rectangular in form. As before, in embodiments, the inter-phase delay can be larger than the width of the positive or negative phase. In embodiments, the inter-phase delay can be at least about 3 times larger than the width of the positive or negative phase, and in embodiments it can be at least about 5 times the width of the positive or negative phase. Pulse-to-pulse time delay 508 separates the first pulse 521 and the second pulse 523, pulse-to-pulse delay 510 separates pulse 523 and pulse 525, and pulse-to-pulse delay 512 separates pulse 525 and pulse 527. The schematic illustration in FIG. 5 shows a decreasing sequence of pulse-to-pulse delays over time; thus pulse-to-pulse delay 512 is smaller than pulse-to-pulse delay 510, and pulse-to-pulse delay 510 is smaller than pulse-to-pulse delay 508.

In embodiments, the sequence of decreasing delays follows at least an arithmetical progression, e.g., the magnitude of the difference between one pulse-to-pulse delay and its immediate predecessor pulse-to-pulse delay is at least a non-zero constant. In embodiments, the sequence of decreasing delays follows at least a geometric progression, e.g., the ratio of one pulse-to-pulse delay to its immediate predecessor pulse-to-pulse delay is smaller than or equal to a constant less than 1. In embodiments, the magnitude of the difference between one pulse-to-pulse delay and its immediate predecessor in a decreasing sequence of pulse-to-pulse delays is at least about 10 microseconds, while in other embodiments it is at least about 100 microseconds. In embodiments, the ratio of one pulse-to-pulse delay to its immediate predecessor in a decreasing sequence of delays is less than about 0.9. In embodiments, the pulse-to-pulse delay sequentially follows a decreasing pattern for at least one-third of the total number of such delays between adjacent pulses in the pulse train.

Figure 6:
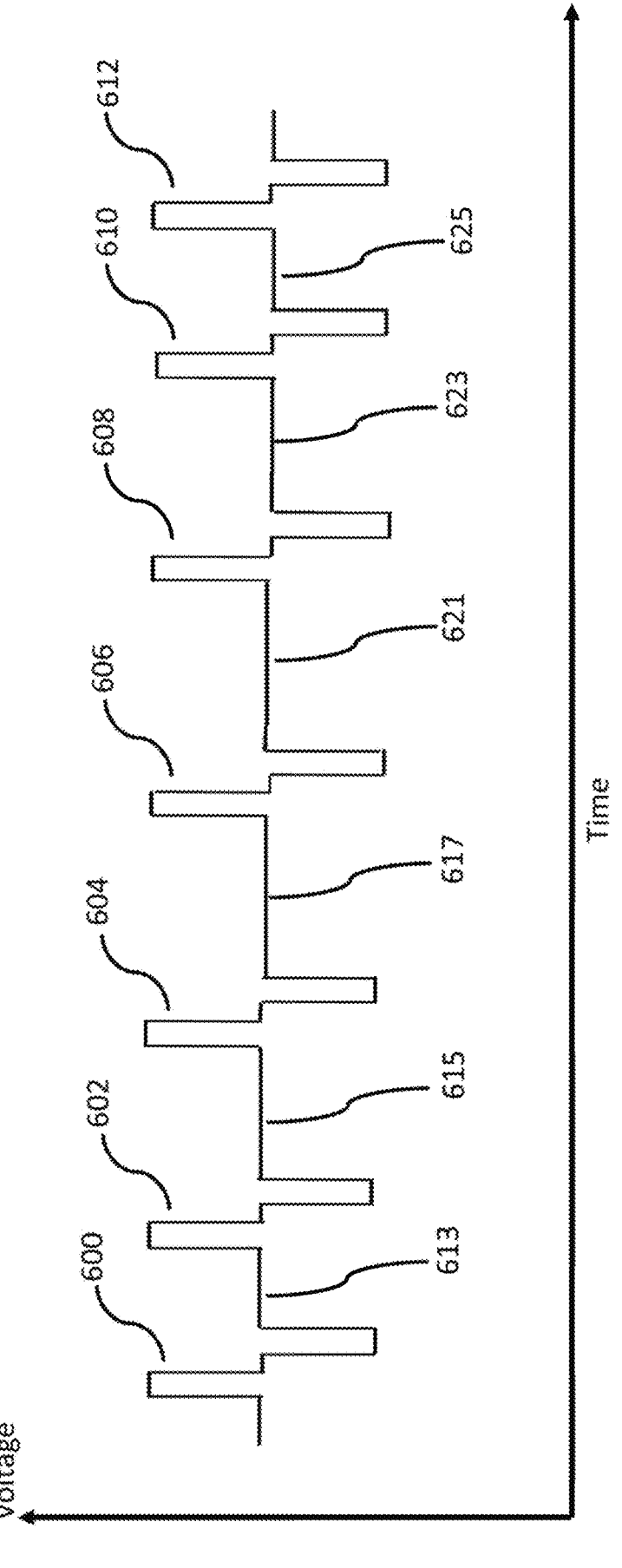
FIG. 6 illustrates an embodiment of a pulse train of the present disclosure having both an increasing sequence of pulse-to-pulse delays and a decreasing sequence of pulse-to-pulse delays.

FIG. 6 illustrates an embodiment of a pulse train of the present disclosure having both an increasing sequence of pulse-to-pulse delays and a decreasing sequence of pulse-to-pulse delays. The figure shows 7 biphasic pulses 600, 602, 604, 606, 608, 610 and 612. Each biphasic pulse has a positive phase, a negative phase, and an inter-phase delay. As before, the pulse train shown has pulses with each phase substantially rectangular in form. In embodiments, the inter-phase delay can be larger than the width of the positive or negative phase. In embodiments, the inter-phase delay can be at least about 3 times larger than the width of the positive or negative phase, and in embodiments, it can be at least about 5 times the width of the positive or negative phase. Pulses 600 and 602 are separated by a pulse-to-pulse delay 613, pulses 602 and 604 are separated by a pulse-to-pulse delay 615, pulses 604 and 606 are separated by a pulse-to-pulse delay 617, pulses 606 and 608 are separated by a pulse-to-pulse delay 621, pulses 608 and 610 are separated by a pulse-to-pulse delay 623, and pulses 610 and 612 are separated by a pulse-to-pulse delay 625. The pulse-to-pulse delays 613, 615, 617 represent a sequence of increasing pulse-to-pulse delays, and the pulse-to-pulse delays 621, 623, and 625 represent a sequence of decreasing pulse-to-pulse delays. In embodiments, the sequence of increasing or decreasing pulse-to-pulse delays follows at least an arithmetical progression, e.g., the magnitude of the difference between one pulse-to-pulse delay and its immediate predecessor is at least a non-zero constant. In embodiments, the sequence of increasing or decreasing pulse-to-pulse delays follows at least a geometric progression, e.g., the ratio of one pulse-to-pulse delay to its immediate predecessor is at least a constant greater than 1 in the case of a sequence of increasing pulse-to-pulse delays, or it is smaller than or equal to a constant less than 1 in the case of a sequence of decreasing pulse-to-pulse delays. In embodiments, the difference between one pulse-to-pulse delay and its immediate predecessor in an increasing sequence of pulse-to-pulse delays is at least about 10 microseconds, while in other embodiments it is at least about 100 microseconds. In embodiments, the ratio of one pulse-to-pulse delay to its immediate predecessor in an increasing sequence of delays is at least about 1.1. In embodiments, the magnitude of the difference between one pulse-to-pulse delay and its immediate predecessor in a decreasing sequence of pulse-to-pulse delays is at least about 10 microseconds, while in other embodiments it is at least about 100 microseconds. In embodiments, the ratio of one pulse-to-pulse delay to its immediate predecessor in a decreasing sequence of pulse-to-pulse delays is less than about 0.9. In embodiments, in a given pulse train, the pulse-to-pulse delay sequentially follows an increasing pattern for at least one-third of the total number of such delays between adjacent pulses and follows a decreasing pattern for at least one-third of the total number of such delays between adjacent pulses.

In embodiments, the pulse widths of the waveforms described herein can range from approximately 0.5 microseconds to approximately 150 microseconds, including all values and ranges therebetween. In embodiments, the inter-phase delay can range from approximately 5 microseconds to approximately 3 milliseconds, including all values and ranges therebetween. In embodiments, the pulse-to-pulse delay can range from approximately 15 microseconds to approximately 500 milliseconds, including all values and ranges therebetween.

FIG. 7 illustrates a trapezoidal biphasic voltage pulse with pulse width and pulse base highlighted, according to embodiments. The trapezoidal voltage pulse shown in FIG. 7 has a positive phase 703 and a negative phase 705 separated by an inter-phase delay 707. Thus, a complete trapezoidal biphasic pulse comprises a positive trapezoidal phase, a negative trapezoidal phase, and a delay between the positive and negative phases. The pulse width of the trapezoidal pulse can be the width of one phase of the pulse where the voltage has a value greater than about 70% of the maximum amplitude of that phase. In the figure, this is marked by the time interval 712 where the positive phase 703 has a value that is greater than or equal to the value indicated by line 703, which marks 70% of the value of the maximum value 710 (i.e., 70% of the amplitude value). In the embodiment shown, the pulse width is equal or approximately equal in the positive and negative phases. In embodiments, the inter-phase delay can be larger than the pulse width of the positive or negative phase. In embodiments, the inter-phase delay can be at least about 3 times larger than the pulse width of the positive or negative phase, and in embodiments it can be at least about 5 times the pulse width of the positive or negative phase.

In embodiments, the corners of the pulses (such as those indicated by 723 and 725 in the figure) can have a rounded shape (not shown). Furthermore, the base width of the pulse is indicated by 715 in FIG. 7. This represents the time interval 715 for which one phase of the pulse has a value larger than 5% of the magnitude of the maximum value 710, as indicated by line 712. In embodiments, the base width of the trapezoidal pulse can be greater than the pulse width by up to about 6 microseconds.

In embodiments, pulse trains can comprise a sequence of trapezoidal pulses. FIG. 8 illustrates an embodiment of a trapezoidal pulse train of the present disclosure with an increasing sequence of pulse-to-pulse delays. The figure shows four trapezoidal pulses 800, 802, 804 and 806. Each complete biphasic pulse, such as for example 800, has a positive phase (indicated by 808) and a negative phase (indicated by 810), separated by an inter-phase time delay (indicated by 814). The pulse train shown has pulses with each phase trapezoidal in form with pulse width and base width similar to that described with reference to FIG. 7. In embodiments, the inter-phase delay can be larger than the pulse width of the positive or negative phase. In embodiments, the inter-phase delay can be at least about 3 times larger than the pulse width of the positive or negative phase, and in embodiments, it can be at least about 5 times the pulse width of the positive or negative phase. There are time delay intervals, referred to as pulse-to-pulse delays, between successive biphasic pulses. As depicted in FIG. 8, pulse-to-pulse time delay 816 (measured from the end of pulse 800 to the start of pulse 802) separates the first pulse 800 and the second pulse 802, pulse-to-pulse delay 818 separates pulses 802 and 804, and pulse-to-pulse delay 820 separates pulses 804 and 806. The pulse-to-pulse delays can vary over the pulse train and in at least portions of the pulse train follow an increasing or decreasing pattern. The schematic illustration in FIG. 8 shows an increasing sequence of pulse-to-pulse delays over time; thus, pulse-to-pulse delay 818 is larger than pulse-to-pulse delay 816, and pulse-to-pulse delay 820 is larger than pulse-to-pulse delay 818.

In embodiments, the sequence of increasing pulse-to-pulse delays follows at least an arithmetical progression, e.g., the difference between one pulse-to-pulse delay and its immediate predecessor pulse-to-pulse delay is at least a non-zero constant. In embodiments, the sequence of increasing delays follows at least a geometric progression, e.g., the ratio of one pulse-to-pulse delay to its immediate predecessor pulse-to-pulse delay is at least a constant greater than 1. In embodiments, the difference between one pulse-to-pulse delay and its immediate predecessor in an increasing sequence of pulse-to-pulse delays is at least about 10 microseconds, while in other embodiments it is at least about 100 microseconds. In embodiments, the ratio of one pulse-to-pulse delay to its immediate predecessor pulse-to-pulse delay in an increasing sequence of delays is at least about 1.1. In embodiments, the pulse-to-pulse delay sequentially follows an increasing pattern for at least one-third of the total number of such delays between adjacent pulses in the pulse train.

FIG. 9 illustrates an embodiment of a trapezoidal pulse train of the present disclosure with a decreasing sequence of pulse-to-pulse delays. The figure shows a biphasic voltage pulse train as a time sequence with four pulses 900, 902, 904 and 906. Each complete biphasic pulse, such as for example 900, has a positive phase (indicated by 908) and a negative phase (indicated by 910) separated by an inter-phase time delay (indicated by 913). The pulse train shown has pulses with each phase trapezoidal in form with pulse width and base width similar to that described with reference to FIG. 7. In embodiments, the inter-phase delay can be larger than the pulse width of the positive or negative phase. In embodiments, the inter-phase delay can be at least about 3 times larger than the pulse width of the positive or negative phase, and in embodiments, it can be at least about 5 times the pulse width of the positive or negative phase. Pulse-to-pulse time delay 915 separates the first pulse 900 and the second pulse 902, pulse-to-pulse delay 917 separates pulse 902 and 904, and pulse-to-pulse delay 919 separates pulse 904 and 906. The schematic illustration in FIG. 9 shows a decreasing sequence of pulse-to-pulse delays over time; thus pulse-to-pulse delay 917 is smaller than pulse-to-pulse delay 915, and pulse-to-pulse delay 919 is smaller than pulse-to-pulse delay 917.

In embodiments, the sequence of decreasing pulse-to-pulse delays follows at least an arithmetical progression, e.g., the magnitude of the difference between one pulse-to-pulse delay and its immediate predecessor pulse-to-pulse delay is at least a non-zero constant. In embodiments, the sequence of decreasing pulse-to-pulse delays follows at least a geometric progression, e.g., the ratio of one pulse-to-pulse delay to its immediate predecessor pulse-to-pulse delay is smaller than or equal to a constant less than 1. In embodiments, the magnitude of the difference between one pulse-to-pulse delay and its immediate predecessor in a decreasing sequence of pulse-to-pulse delays is at least about 10 microseconds, while in other embodiments it is at least about 100 microseconds. In embodiments, the ratio of one pulse-to-pulse delay to its immediate predecessor in a decreasing sequence of pulse-to-pulse delays is less than about 0.9. In embodiments, the pulse-to-pulse delay sequentially follows a decreasing pattern for at least one-third of the total number of such delays between adjacent pulses in the pulse train.

FIG. 10 illustrates an embodiment of a trapezoidal pulse train of the present disclosure having both an increasing sequence of pulse-to-pulse delays and a decreasing sequence of pulse-to-pulse delays. The figure shows 7 biphasic pulses 1001, 1002, 1003, 1004, 1005, 1006 and 1007. Each complete biphasic pulse has a positive phase, a negative phase, and an inter-phase delay. As before, the pulse train shown has pulses with each phase trapezoidal in form. In some embodiments, the inter-phase delay can be larger than the pulse width of the positive or negative phase. In embodiments, the inter-phase delay can be at least about 3 times larger than the pulse width of the positive or negative phase, and in embodiments, it can be at least about 5 times the pulse width of the positive or negative phase. Pulses 1001 and 1002 are separated by a pulse-to-pulse delay 1010, pulses 1002 and 1003 are separated by a pulse-to-pulse delay 1012, pulses 1003 and 1004 are separated by a pulse-to-pulse delay 1014, pulses 1004 and 1005 are separated by a pulse-to-pulse delay 1017, pulses 1005 and 1006 are separated by a pulse-to-pulse delay 1019, and pulses 1006 and 1007 are separated by a pulse-to-pulse delay 1021. The pulse-to-pulse delays 1010, 1012 and 1014 represent a sequence of increasing pulse-to-pulse delays, and the pulse-to-pulse delays 1017, 1019 and 1021 represent a sequence of decreasing pulse-to-pulse delays. In embodiments, the sequence of increasing or decreasing pulse-to-pulse delays follows at least an arithmetical progression, e.g., the magnitude of the difference between one pulse-to-pulse delay and its immediate predecessor is at least a non-zero constant. In embodiments, the sequence of increasing or decreasing pulse-to-pulse delays follows at least a geometric progression, e.g., the ratio of one pulse-to-pulse delay to its immediate predecessor is at least a constant greater than 1 in the case of a sequence of increasing pulse-to-pulse delays, or it is smaller than or equal to a constant less than 1 in the case of a sequence of decreasing pulse-to-pulse delays. In embodiments, the ratio of one pulse-to-pulse delay to its immediate predecessor in an increasing sequence of pulse-to-pulse delays is at least about 1.1. In embodiments, the ratio of one pulse-to-pulse delay to its immediate predecessor in a decreasing sequence of pulse-to-pulse delays is less than about 0.9. In embodiments, the magnitude of the difference between one pulse-to-pulse delay and its immediate predecessor in an increasing or a decreasing sequence of pulse-to-pulse delays is at least about 10 microseconds, while in other embodiments it is at least about 100 microseconds. In embodiments, in a given pulse train, the pulse-to-pulse delay sequentially follows an increasing pattern for at least one-third of the total number of such delays between adjacent pulses and follows a decreasing pattern for at least one-third of the total number of such delays between adjacent pulses.

In embodiments, the pulse widths of the trapezoidal waveforms described herein can range from approximately 0.5 microseconds to approximately 150 microseconds, including all values and ranges therebetween. The inter-phase delay can range from approximately 5 microseconds to approximately 3 milliseconds, including all values and ranges therebetween. The pulse-to-pulse delay can range from approximately 15 microseconds to approximately 500 milliseconds, including all values and ranges therebetween.

FIG. 11 illustrates a waveform with multiple packets of pulse trains with packet delays across the series of packets, according to embodiments. In some embodiments, the waveform illustrated in FIG. 11 can be applied to an electrode set including electrode subsets that are oppositely polarized (e.g., a first subset including one or more electrodes to be energized with a first polarity paired with a second subset including one or more electrodes to be energized with a second, opposite, polarity). In some embodiments, during application of the waveform, the electrode subsets can alternate in polarity, e.g., in the case of biphasic pulses. The figure shows multiple pulse trains or packets 1102, 1104 and 1106. Each pulse train or packet, such as 1102, 1104, or 1106, comprises a series of pulses 1100 that may be similar to that described in FIGS. 4-6 and 8-10, in various embodiments. Packet delays separate one pulse packet from the next. For example, packet delay 1111 separates packets 1102 and 1104, and packet delay 1113 separates packets 1104 and 1106. In embodiments, the packet delays can be non-constant or varying across the series of packets. In embodiments, the number of pulses in each packet can be non-constant or varying across packets. In embodiments, each packet delay can range from approximately 300 milliseconds to approximately 12 seconds, including all values and ranges therebetween.

In embodiments, the number of complete biphasic pulses in each pulse train of the present disclosure can range from 1 to about 30, including all values and ranges therebetween, while the number of pulse packets can range from 1 to about 20, including all values and ranges therebetween.

The waveforms of the present disclosure can be applied to more than one electrode set in various formats. For example, FIG. 12 illustrates sequenced delivery of a waveform in the form of a multiplicity of pulse packets delivered to a multiplicity of electrode pairs or electrode sets. In FIG. 12, pulse packets 1202 and 1208 represent two pulse packets applied to a first electrode set. Each pulse packet such as 1202 or 1208 comprises a pulse train 1201. The packet delay between packets 1202 and 1208 is the sum of time intervals 1213 and 1215 in FIG. 12. During this packet delay, pulse packets 1204 and 1206 can be sequentially applied respectively to a second electrode set and a third electrode set. In embodiments, the packet delays (or intervals contained therein) between successive packets being applied to one or more electrode sets can vary between successive packets applied to those electrode sets. For example, each of the time intervals such as 1213 and 1215 that comprise the packet delay between successive packets 1202 and 1208 applied to a first electrode set are not constant over the entire pulse waveform but can vary between successive packets applied to the first electrode set. Subsequently, after the second packet 1208 is applied to the first electrode set, packets 1210 and 1212 are respectively applied to the second and third electrode set. Alternatively, packets 1210 and 1212 can be applied to different electrode sets or applied to electrode sets in a different order. For example, packets 1210 and 1212 can be applied to the third electrode set and the second electrode set, respectively, or packets 1210 and 1212 can be applied to a fourth electrode set and a fifth electrode set in any order, or packets 1210 and 1212 can be applied to a fourth electrode set and the second electrode set in any order, or packets 1210 and 1212 can be applied to the third electrode set and a fourth electrode set in any order. It should be apparent that the process of delivery extends to multiple numbers of pulse packets and multiple numbers of electrode sets, without limitation to the specific number depicted in FIG. 12. In embodiments, the number of distinct electrode sets to which such a waveform is applied can range from 1 to about 20, including all values and ranges therebetween.

Other methods and sequences of waveform delivery may be constructed according to the teachings herein. For example, FIG. 13 illustrates sequenced delivery of a pulse train of a waveform in the form of individual pulses of a pulse train respectively delivered to a multiplicity of electrode pairs in interleaved fashion. In the figure, biphasic pulses 1301, 1307 and 1313 represent three complete biphasic pulses of a pulse train applied to a first electrode set. Time interval or pulse-to-pulse delay 1317 separates pulses 1301 and 1307, while the time interval or pulse-to-pulse delay 1319 separates pulses 1307 and 1313. During the time interval or delay 1317, biphasic pulses 1303 and 1305 are respectively applied to a second electrode set and a third electrode set. During the time interval or delay 1319, biphasic pulses 1309 and 1311 are respectively applied to additional electrode sets (e.g., applied to a second electrode set and a third electrode set in any order, or to a fourth electrode set and a fifth electrode set in any order, or a fourth electrode set and the second electrode set in any order, or the third electrode set and a fourth electrode set in any order). It should be apparent that this process of electrode-interleaved delivery of the pulse train extends to multiple numbers of pulses and pulse-to-pulse delays and multiple numbers of electrode sets, without limitation to the specific number depicted in FIG. 13. In embodiments, the number of distinct electrode sets to which such a waveform is applied can range from 1 to about 20, including all values and ranges therebetween.

Systems, devices, and methods can be configured to deliver pulse waveforms having various sequences of pulses (e.g., monophasic or biphasic pulses), such as any one of the pulse waveforms shown in FIGS. 4-13. In some embodiments, the generator may be configured to store pulse parameters for each pulse (e.g., amplitude, inter-phase delay, pulse width, etc.) as well as a pulse sequence information (e.g., as reflected in pulse sequence tables as shown in FIGS. 18-21) including (1) the electrode pairings or subsets to be activated for each biphasic pulse and (2) pulse-to-pulse delays (e.g., the delay between adjacent pulses). As shown in FIG. 18, the number of biphasic pulses (P1, P2, . . . PN), the electrode pairings (EP1, EP2 . . . EPN), and/or the pulse-to-pulse delay values (D1, D2, . . . DX) may vary over the pulse sequence, according to any suitable pattern. In some embodiments, a total number of biphasic pulses in the pulse sequence may be in a range between about 1 to about 200, inclusive of all values and subranges therebetween. In some embodiments, the pulse-to-pulse delay may be between about 15 microseconds to about 500 milliseconds, inclusive of all values and subranges therebetween. In some embodiments, the pulse-to-pulse delay may be at least about 0.5 milliseconds. In some embodiments, each of the biphasic pulses may have a pulse width in a range of about 0.5 microseconds to about 150 microseconds, inclusive of all values and subranges therebetween, including, for example, between about 0.5 microseconds and 20 microseconds. In some embodiments, each biphasic pulse may include an inter-phase delay in a range of about 5 microseconds to about 3 milliseconds, inclusive of all values and subranges therebetween. In some embodiments, a signal generator (or pulse generator) may be configured to send a signal including sequence information to a signal router including the electrode pairings and pulse-to-pulse delay between biphasic pulses such that the router can set switches in a system for delivering pulsed field ablation, according to the sequence information.

In some embodiments, pulses can be delivered to each electrode set according to a pulse sequence associated with that electrode set. In other words, pulses having a sequence of increasing and/or decreasing pulse-to-pulse delays, as described herein, can be applied to each electrode set. Moreover, different sequences can be applied to different electrode sets, and pulses being applied to one electrode set can be interleaved with pulses being applied to another electrode set. For example, the system may include a first electrode set configured to be activated according to a first pulse sequence (e.g., including a first sequence of pulse-to-pulse delays) and a second electrode set configured to be activated according to a second pulse sequence (e.g., including a second sequence of pulse-to-pulse delays). In some embodiments, the second pulse sequence may be different than the first pulse sequence such that each electrode set is activated with different patterns of delay. In some embodiments, pulses applied through the first electrode set may be interleaved with pulses applied through the second electrode set. In other words, pulses can be delivered to the second electrode set during delay periods between pulses of the first electrode set (e.g., pulse-to-pulse delays or packet delays), and vice versa. For example, pulses applied to the second electrode set can occur during pulse-to-pulse delays (e.g., delays between biphasic pulses) applied to the first electrode set, as described with reference to FIG. 13 above. As another example, pulses applied to the second electrode set can occur during packet delays between pulse packets applied to the first electrode set, as described with reference to FIG. 12 above.

FIG. 19 shows an example pulse sequence represented in a table format, which includes pulses (P1-PN) that are to be delivered to one pair of electrodes E1, E2. While single electrodes are paired in this example, more generally different electrode subsets (each subset including one or more electrodes) can be paired or oppositely polarized for purposes of pulse delivery. In some embodiments, a total number of pulses in the sequence may be in a range between about 5 to about 200 biphasic pulses, inclusive of all values and subranges therebetween, including, for example, about 10 to about 120 pulses. The table can include delays-to-next pulse, which can include pulse-to-pulse delays and/or packet delays, as described herein. In some embodiments, the delays-to-next pulse may have values in a range between about 15 microseconds and about 12 seconds, inclusive of all values and subranges therebetween. In some embodiments, the pulse-to-pulse delay may increase (e.g., monotonically or not monotonically) over a first predetermined number of pulses (e.g., P1-P5) and decrease (e.g., monotonically or not monotonically) over a second predetermined number of pulses (e.g., P6-P10). For example, the pulse-to-pulse delays D1, D2, D3, D4 and D5 may increase in magnitude from D1 to D5. The pulse-to-pulse delays may increase from D1-D5, and then decrease from D5 to D1. In other words, the pulse sequence can include an increasing sequence of pulse-to-pulse delays followed by a decreasing sequence of pulse-to-pulse delays. While the decreasing sequence of pulse-to-pulse delays is shown as immediately following the increasing sequence of pulse-to-pulse delays, it can be appreciated that the decreasing sequence of pulse-to-pulse delays can follow the increasing sequence of pulse-to-pulse delays with there being one or more pulses (e.g., pulse-to-pulse delays and/or packet delays) that separate the increasing sequence of pulse-to-pulse delays and the decreasing sequence of pulse-to-pulse delays. In some embodiments, the increasing sequence of delays and the decreasing sequence of delays can be symmetrical, e.g., have the same number of delays with the same delay periods but in reverse order. In other embodiments, the decreasing sequence of delays and the increasing sequence of delays can be asymmetrical. In some embodiments, the increasing and decreasing sequence of pulses (e.g., P1-P10) constitute a first packet, and D6 may represent a packet delay between the first packet and a subsequent packet. In some embodiments, the delay D6 may be substantially longer (e.g., at least about two times longer) than the pulse-to-pulse delays D1-D5. In some embodiments, the pulse-to-pulse delay may increase/decrease over any suitable number of biphasic pulses, including over at least three pulses. In other embodiments, the pulse-to-pulse delays can include a sequence of decreasing delays followed by a sequence of increasing delays. In some embodiments, the decreasing sequence of delays and the increasing sequence of delays can be symmetrical, e.g., have the same number of delays with the same delay periods but in reverse order. In other embodiments, the decreasing sequence of delays and the increasing sequence of delays can be asymmetrical. In some embodiments, the pulse-to-pulse delays may increase/decrease by a predetermined factor between pulses. In some embodiments, the pulse-to-pulse delays may increase/decrease by a set duration. For example, subsequent pulse-to-pulse delays in a sequence can be longer than or shorter than previous pulse-to-pulse delays in that sequence by a set duration. In some embodiments, the pulse-to-pulse delays may increase/decrease according to any suitable pattern, including at arbitrarily set values. In some embodiments, the pulse pattern of P1-P11 may be repeated a plurality of times. While FIG. 19 shows the pulse sequence being delivered through one pair of electrodes E1, E2, in some embodiments, the pulse sequence may be delivered through a plurality of electrode pairings and/or a plurality of subsets of electrodes, e.g., by interleaving pulses between different electrode sets.

FIG. 20 shows an example pulse sequence represented in a table format, which includes pulses (P1-PN) that are to be delivered to multiple pairs of electrodes. In this example, the multiple pairs of electrodes can include pairs of electrodes selected from three electrodes E1, E2, E3. Therefore, as shown in the table, for each biphasic pulse, a pair from the plurality of electrodes E1, E2, and E3 may be activated. The table can include delays-to-next pulse, which can include pulse-to-pulse delays and packet delays, as described herein. In some embodiments, the delays-to-next pulse may have values in a range between about 15 microseconds and about 12 seconds, inclusive of all values and subranges therebetween. Additionally, in some embodiments, the delays-to-next pulse can include packet delays (e.g., delays between packets of pulses) between about 100 milliseconds and about 5 seconds, inclusive of all values and subranges therebetween.

In some embodiments, the pulse-to-pulse delay may increase (e.g., monotonically or not monotonically) over a first predetermined number of pulses (e.g., P1-P6) and decrease (e.g., monotonically or not monotonically) over a second predetermined number of pulses (e.g., P7-P12), and increase (e.g., monotonically or not monotonically) over a third predetermined number of pulses (e.g., P13-P18). For example, the pulse-to-pulse delays D1, D2, D3, D4, D5, D6 may increase in magnitude from D1 to D6. In some embodiments, the pulse-to-pulse delays may increase/decrease by a predetermined factor between pulses. In some embodiments, the pulse-to-pulse delays may increase/decrease by a set duration. For example, subsequent pulse-to-pulse delays in a sequence can be longer than or shorter than previous pulse-to-pulse delays in that sequence by a set duration. In some embodiments, the pulse-to-pulse delays may increase/decrease according to any suitable pattern, including at arbitrarily set values.

As described above, pulses can be delivered to each electrode pair according a specific sequence of pulse-to-pulse delays, with the same or different sequences being applied to each electrode set. As shown, the first pair of electrodes E1, E2 includes a first sequence of pulse-to-pulse delays, and the second pair of electrodes E1, E3 has a second sequence of pulse-to-pulse to pulse delays. The first sequence of pulse-to-pulse delays differs from the second sequence of pulse-to-pulse delays (e.g., the first sequence increases in duration over each pulse, while the second sequence decreases in duration over each pulse).

In some embodiments, the pair of electrode subsets activated in the pulse table may change after an increasing portion of the delay sequence (e.g. a portion where the delays increase), after a decreasing portion of the sequence (e.g., a portion where the delays decrease), or after a combination of an increasing portion or decreasing portion of the sequence (e.g., a portion including an increase in delays and a decrease in delays). In some embodiments, the paired electrode subsets may change after a predetermined number of pulses (e.g., between 1 and 20 pulses, inclusive of all values and subranges therebetween). In the example shown, the pair of electrodes activated switches after either 6 or 7 biphasic pulses, or after the completion of an increasing portion or decreasing portion of the sequence. For example, a first pair of electrodes E1, E2 may be activated for the pulses P1-P6, a second pair of electrodes E1, E3 may be activated for pulses P7-P13, and a third pair of electrodes E2, E3 may be activated for pulses P14-P20. Over the entire pulse train, a given electrode pairing can occur irregularly or in non-periodic manner.

FIG. 21 shows an example pulse sequence represented in table format, which includes pulses P1-PN configured to be delivered to multiple pairs of electrodes. The multiple pairs of electrodes can include pairs of electrodes selected from four electrodes E1, E2, E3, E4. In some embodiments, a total number of pulses in the sequence may be in a range of about 10 pulses to about 150 pulses, inclusive of all values and subranges therebetween. In some embodiments, the delays-to-next pulse may have values in a range between about 15 microseconds and about 12 seconds, inclusive of all values and subranges therebetween.

In some embodiments, the pulse-to-pulse delays D1, D2, D3, D4, and D5 may vary across the pulse sequence, but the pulse-to-pulse delays for those pulses that are delivered to a particular electrode pair can increase and/or decrease according to the sequence. As shown in FIG. 21, the pair of electrodes activated can switch from pulse to pulse, such that the pulses are interleaved between multiple electrode pairs. For example, the pulse sequence may start with a first pair of electrodes E1, E2, followed by a second pair of electrodes E3, E4. The third pulse P3 engages E1, E2 again, while the next occurrence of the pair E1, E2 in pulse P6 is preceded by fourth pulse P4 engaging E2, E4 and fifth pulse P5 engaging E1, E3. In some embodiments, the first pair of electrodes E1, E2 and the second pair of electrodes E3, E4 may alternate over a sub-sequence (e.g., a portion of the sequence) of pulses. In some embodiments, the pulse sequence may include a constant pulse-to-pulse delay following pulses that are delivered to a first pair of electrodes, and changing pulse-to-pulse delays following pulses that are delivered to a second pair of electrodes. Similarly, decreasing delays can also be applied to delays following the activation of one electrode pair, while delays following the activation of another electrode pair remain constant. Interleaving pulses between multiple electrode pairs or electrode sets may decrease a total amount of time needed for a procedure (e.g., to deliver sufficient energy through the electrode sets to tissue to ablate the tissue). For example, applying pulses for one set of electrodes during delay periods for another set of electrodes can take advantage of such delay periods and avoid inefficiencies. In other words, applying pulses through one set of electrodes during the delay periods of a different set of electrodes allows pulses to be delivered to one set of electrodes while the other set of electrodes is being reset for its next pulse. This increases the efficiency with which the system can deliver the total number of pulses.

While FIGS. 19-21 show example pulse sequence patterns, it should be appreciated that any subset of electrodes may be activated with any suitable pattern of pulse-to-pulse delays and/or packet delays to generate a desired electromagnetic field exposure from the ablation device.

Generator and Control Circuitry

Pulse waveforms as described herein can be delivered to devices including sets of electrodes using a generator and control circuitry, as described herein. FIG. 14 is a schematic illustration of a generator system including a pulse generator and a signal router for delivery of a pulsed field ablation waveform to a medical device, according to embodiments.

The signal or pulse generator 1400 may be configured to generate pulse waveforms for irreversible electroporation of tissue. The signal generator (or pulse generator) 1400 may be a voltage pulse waveform generator and deliver a pulse waveform to a set of electrodes of the ablation device 1419. The signal generator (or pulse generator) 1400 may generate and deliver several types of signals including, but not limited to, radiofrequency (RF), direct current (DC) impulses, stimulus range impulses, and/or hybrid electrical impulses. For example, the signal generator (or pulse generator) 1400 may generate monophasic (DC) pulses and/or biphasic (whether DC or AC) pulses.

The signal generator (or pulse generator) 1400 may include or be coupled to a processor, memory, a set of electrode channels 1415, energy source, signal router 1402, and/or user interface. One or more signal generator components may be coupled using a communication bus. The signal router 1402 can include control circuitry, inclusive of at least a portion of the electrode channels 1415 that output the biphasic waveform. The processor may incorporate data received from one or more of memory, electrode channels 1415, energy source(s), signal router 1402, user interface, and/or the device 1419 to determine the parameters (e.g., amplitude, width, duty cycle, timing, etc.) of the voltage pulse waveform to be generated by the signal generator (or pulse generator) 1400. In embodiments, the processor can recognize the type of device 1419 that is connected to the electrode channels 1415 and automatically select a predetermined waveform or pulse sequence appropriate for that device from the memory. The memory may further store instructions (e.g., pulse parameters and/or pulse sequence information) to cause the processor to execute modules, processes and/or functions associated with the system, such as pulse waveform generation and delivery, electrode channel configuration, fault testing, and/or energy discharge. For example, the memory may be configured to store anode/cathode configuration data, electrode channel configuration data, pulse waveform data, pulse sequence data, fault data, energy discharge data, patient data, clinical data, procedure data, and/or the like.

In some embodiments, an energy source may be configured to convert and supply energy to a set of electrodes coupled to the signal generator (or pulse generator) 1400. The energy source of the signal generator (or pulse generator) 1400 may include a DC power supply and be configured as an AC/DC switcher. In some embodiments, an energy source of the signal generator (or pulse generator) 1400 may deliver rectangular-wave pulses. In some of these embodiments, the energy source may be configured to store energy. For example, the energy source may include one or more capacitors to store energy from a power supply.

In some embodiments, the signal generator (or pulse generator) may include a user interface configured to receive user input (e.g., inputs for procedure selection, device selection or device electrode selection). In some embodiments, the signal generator (or pulse generator) may prevent a user from modifying pulse sequences and/or pulse parameters. Enabling the user to modify pulse sequences and/or pulse parameters may lead to unpredictable and/or uncontrolled results, impacting the safety and/or effectiveness of a procedure. The signal generator (or pulse generator) may be configured to determine (e.g., automatically) the pulse sequence and/or pulse parameters based on the procedure selection and/or device selection or based on the type of device coupled to the generator. The user interface may include an input device for user interaction (e.g., touch screen and graphic display). As another example, operator control of an input device having one or more buttons, knobs, dials, switches, trackball, touch surface, and/or the like, may generate a control signal to the signal generator (or pulse generator) 1400 and/or the device 1419.

In some embodiments, the processor may be any suitable processing device configured to run and/or execute a set of instructions or code and may include one or more data processors, image processors, graphics processing units, physics processing units, digital signal processors, and/or central processing units. The processor may be, for example, a general purpose processor, Field Programmable Gate Array, an Application Specific Integrated Circuit (ASIC), and/or the like. The processor may be configured to run and/or execute application processes and/or other modules, processes and/or functions associated with the system and/or a network associated therewith (not shown).

In some embodiments, the memory may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory may store instructions to cause the processor to execute modules, processes and/or functions associated with the system, such as pulse waveform generation, electrode channel configuration, fault detection, energy discharge, etc.

FIG. 14 shows a pulse generator 1400 in communication with a signal router 1402. The signal router 1402 incorporates a control and timing unit such as, for example, a microcontroller. In embodiments, the pulse generator 1400 can incorporate a microcontroller or a Field Programmable Gate Array (FPGA) for timing control of pulses and/or pulse trains, and in embodiments, the pulse generator 1400 can incorporate at least one FPGA and at least one microcontroller. In embodiments, the signal router 1402 can incorporate an FPGA or a microcontroller.

Communication signals, in either direction, between the signal router 1402 and the pulse generator 1400 are passed through at least one communication channel 1406; in embodiments, there can be one or multiple such channels for communication. In embodiments, there can also be a separate connection (not shown) between the pulse generator 1400 and the signal router 1402 for passing a trigger signal from the signal router 1402 to the pulse generator 1400. In embodiments, the communication channel 1406 can also serve to pass a trigger signal from the signal router 1402 to the pulse generator 1400. The communication channel 1406 can define one or more requests for specific pulses or pulse trains from the signal generator (or pulse generator) 1400 based on a pre-determined set of communication signals or words. When a trigger signal (corresponding to a request for a defined pulse or pulse train) is sent to the pulse generator 1400 from the signal router 1402, the pulse generator 1400 generates the appropriate pulse or pulse train and sends it to the signal router 1402 via a high voltage link 1410. The signal router 1402 controls the opening and closing of appropriate switches to route the incoming pulse or pulse train from the pulse generator 1400 to the appropriate set or subset of channels 1415 for delivery of the pulsed waveform to a desired medical device 1419, e.g., for tissue ablation. In embodiments, the number of channels 1415 can range from 2 to about 20, including all values and ranges therebetween. In embodiments, the outputs of the channels 1415 can be connected to appropriate medical device electrodes, and in embodiments, at least one of the channels 1415 can be connected to a reference electrode patch, e.g., for placement on the body surface of a subject. In embodiments where only two output channels are needed, there may not be a need for signal router 1402 and in this case, only the pulse generator 1400 comprises the generator system. In embodiments, either the signal router 1402 or the pulse generator 1400, or both, can include transformers on the output path for appropriate electrical isolation. In embodiments, the signal router 1402 can include relays that are closed only during ablation delivery, e.g., as additional protection to ensure output occurs only when desired. In embodiments, the generator system can be modular so that either the pulse generator 1400 or the signal router 1402 can be swapped for a different similar piece, for instance, as may be needed for repair or replacement. In embodiments, the pulse generator 1400 and the signal router 1402 can be separate units or boxes with appropriate cabling connections between the two, while in other embodiments, the pulse generator 1400 and the signal router 1402 can be housed as separate sets of electronic boards within a single unit or box. In embodiments, the signal router 1402 and/or the pulse generator 1400 may have a user interface for user input of parameters, such as, for example, voltage amplitude, medical device type, number of electrodes or electrode sets, and other operational parameters. This user input can be used by the generator system to deliver the appropriate waveform.

In some embodiments, the pulse generator 1400 may be configured to store (e.g., via the memory or processor) pulse parameters for each biphasic pulse (e.g., amplitude, inter-phase delay, pulse width, etc.) as well as pulse sequence information (e.g., tables) including the electrode pairings or subsets to be activated and/or pulse-to-pulse delays. In some embodiments, a particular pulse sequence may be selected (e.g., by a user via the user interface) or pre-programmed based on procedure and/or treatment, and the pulse generator 1400 and the signal router 1402 may be configured to collectively deliver the pulse sequence via the plurality of electrodes. The generator 1400 can be configured to maintain the pulse parameters and pulse sequence information represented as a table of electrode parings for each pulse in the sequence and delays-to-next pulse (e.g., pulse-to-pulse delays and/or packet delays). Then for the operation of the signal router 1402, the pulse parameters can be defined at the base of each pulse (e.g., to account for IGBT turn-on and turn-off times calibrated for set voltage, etc.).

After communication is established or confirmed between the pulse generator 1400 and the signal router 1402 and/or when a desired pulse sequence is selected, in some embodiments, the pulse generator 1400 may send a first signal to the router 1402 including (i) a pulse width of each biphasic pulse and (ii) an inter-phase delay. The inter-phase delay may be a duration between a positive pulse of the biphasic pulse and a negative pulse of the biphasic pulse. In some embodiments, the pulse width and/or inter-phase delay may remain constant across the pulse sequence. In some embodiments, the pulse width and/or the inter-phase delay may vary across the pulse sequence. In some embodiments, the signal generator (or pulse generator) 1400 may be configured to send a second signal to the router 1402, prior to each pulse, assigning an electrode/channel pairing for that respective pulse. The router 1402, in response to receiving the second signal may set a first subset of switches for the positive portion of the biphasic pulse. In some embodiments, the router 1402 may be configured to send an acknowledgment signal to the generator 1400 after the first subset of switches are set. In some embodiments, the generator 1400 may be configured to send a pulse signal to the router 1402 upon the generator 1400 receiving the acknowledgment signal. In some embodiments, after the positive duration of the biphasic pulse, the router 1402 may be configured to open the switches during the inter-phase delay, then reverse the first subset of switches to allow the negative duration of the biphasic pulse to occur. After the negative duration of the biphasic pulse occurs, the router 1402 may be configured to open the switches. In some embodiments, the router 1402 may be configured to send a confirmation signal to the generator 1400 that the biphasic pulse has been delivered. The generator 1400 and router 1402 may be configured to repeatedly communicate the signals described herein to generate a pulse sequence according the pulse sequence information (e.g., table) stored on or accessible to the pulse generator 1400.

In embodiments, once a connected device has been identified, either automatically or by user selection, the pulse generator 1400 can select a corresponding waveform or pulse table (or pulse sequence information) associated with that device. In embodiments, the user selection can include identification of the electrodes to be activated for ablation. The pulse generator can send the pulse table, or the identification of the pulse table (for example, Pulse Table 7) to the router 1402. In embodiments, the router can incorporate an FPGA that stores a collection of pulse tables. Upon receiving the table identification, the appropriate pulse table in the FPGA is automatically selected for ablation delivery. In embodiments, the pulse table in the router FPGA contains the sequence of electrode pairings, while the timing of pulse generation is controlled by the pulse generator which maintains a table of timing information (for example, pulse parameters and delays). The communication channel 1406 can provide timing information to the router to control the closing and opening of appropriate switches for electrode selection for a given pulse. Upon the completion of a pulse, the router steps to the next electrode pairing in the sequence and appropriately resets the electrode channel switches. It should be apparent to one skilled in the art that the information in the pulse table for timing and electrode sequencing can generally be stored between the pulse generator and the router in several different ways (e.g., with one or both storing the pulse table and/or sequence of electrode sets, or a portion thereof), and the implementation can be dictated by, for example, convenience.

FIG. 15 is a schematic illustration of control circuitry for operation of a single channel of a generator system, according to the present disclosure. Voltage terminals 1500 and

1502 respectively represent positive and negative terminals of a high voltage source (for example, a capacitor or a transformer depending on the embodiment). In embodiments, the high voltage source can be a pulse generator. High power switches 1520 and 1522 are connected as shown between the terminals; for example, these can comprise high-power solid-state switches such as, for example, Insulated Gate Bipolar Transistors (IGBT's) or Metal Oxide Field Effect Transistors (MOSFET's). The switches 1520 and 1522 are controlled by respective drive circuits 1508 and 1510 (e.g., forming part of a signal router, such as signal router 1502) that act to turn the switches on or off, and the drive circuits 1508 and 1510 are driven by an FPGA or microcontroller 1506 that controls the timing of opening and closing switches based on a desired waveform output. In embodiments, the specific pulse and/or pulse train details are sent to FPGA or microcontroller 1506 from microcontroller 1513. In embodiments, the path from terminal 1500 to terminal 1522 can include a current-limiting resistor to mitigate any short circuits. Only one of the switches 1520 or 1522 is closed at a given time, while the other one remains open. In this way, the channel output 1518 is connected to either the positive or the negative terminal. For an approximately constant voltage source at the terminals, depending on the rise time or switching time of the switches 1520 and 1522, the shape of the pulse can be rectangular, trapezoidal, or substantially rectangular or trapezoidal. In embodiments, the output path 1518 can incorporate filtering circuitry (not shown) to limit voltage or current spiking that can round the corners of the pulses, as discussed earlier.

By pairing the single-channel topology of FIG. 15 with a second similar channel, a current path and channel pairing can be established for the waveform output between an arbitrary pair of channels connected to separate device electrodes or electrode sets. FIG. 16 illustrates the half bridge topology of two channels of a generator system that can be combined to deliver a pulsed field ablation waveform to a pair of electrodes or electrode sets respectively connected to the two channels, according to embodiments. Output channel 1620 in FIG. 16 is connected to a half bridge topology comprising switches 1603 and 1605, the switches 1603 and 1605 respectively connected to positive terminal 1615 and negative terminal 1617 of a high voltage source. Likewise, output channel 1622 in FIG. 16 is connected to a half bridge topology comprising switches 1609 and 1611, the switches 1609 and 1611 respectively connected to positive terminal 1615 and negative terminal 1617 of the same high voltage source. When switches 1603 and 1611 are closed while 1605 and 1609 are open, a positive voltage pulse is delivered to output channels 1620 and 1622 as a current path is established between the electrodes and the tissue impedance seen between device electrodes connected to channels 1620 and 1622. Likewise, when switches 1605 and 1609 are closed while 1603 and 1611 are open, a negative voltage pulse is delivered to output channels 1620 and 1622. By suitable timing of the opening and closing of the switches, a desired complete biphasic pulse can be generated. In embodiments the opening and the closing of the switches can be controlled by a signal router (e.g., signal router 1402), driven by pulse generation and timing control from the pulse generator 1400.

FIG. 22 illustrates control circuitry for operation of a plurality of electrode channels connected to separate device electrodes, according to an embodiment. The control circuitry is part of a signal router such as 1402 in FIG. 14 that is configured to control the timing of the opening and closing of the switches of the plurality of electrode channels. As described with respect to FIG. 14, the electrode channels (e.g., electrical lines connected to each electrode E1, E2, E3, E4, E5, E6) may be included in or be part of the signal router. The plurality of electrode channels may be coupled to a plurality of output electrodes E1, E2, E3, E4, E5, E6. The electrode channels may include a plurality of upper switches (e.g., IGBT's) U1, U2, U3, U4, U5, U6 and a plurality of lower switches (e.g., IGBT's) L1, L2, L3, L4, L5, L6. In some embodiments, an electrode pairing can include up to 2 anodes and up to 2 cathodes at a time; however, any pairing of electrode subsets (for example, electrode E1 paired with the subset (E2, E3), etc.) can also be used for ablation delivery without departing from the disclosed embodiments herein. For example, arbitrary electrode sets can be paired, with each set comprising one or more electrodes. As examples, ({E1}, {E3, E4}) is a pairing of electrode E1 at one polarity with electrodes E3 and E4 at the opposite polarity, and ({E1, E2}, {E3, E4}) is a pairing of electrodes E1 and E2 at one polarity with electrodes E3 and E4 at the opposite polarity. In some embodiments, a combination of any subset of electrodes may be achieved by adjusting the corresponding upper and/or lower switches. For example, to activate electrode subset ({E2}, {E5, E6}) in in the positive phase of the pulse, upper switch U2 is engaged, along with lower switches L5 and L6. In the negative phase of the pulse, upper switches U5 and U6 are engaged, along with lower switch L2. Other combinations can also be implemented by opening and closing switches, as necessary.

Methods of Operation

FIG. 17 illustrates the operation of the system of the present disclosure for waveform delivery, in an embodiment. When a user enables waveform delivery through a user interface of the generator system (similar to other generator systems described herein, e.g., generator system depicted in FIG. 14), the communication between the signal router of the generator system and the pulse generator of the generator system is checked and confirmed, at 1703. If communication is disabled, a system error is called out, otherwise at 1705, the signal router sends a first message to the pulse generator including the form of the output desired from the pulse generator, i.e., whether a single pulse or an entire pulse train. In embodiments, reception of this message is confirmed by the pulse generator to the signal router. Subsequently, at 1707, the signal router sends a second message to the pulse generator including details of the single pulse or entire pulse train to the pulse generator. In embodiments, reception of this second message is confirmed by the pulse generator to the signal router. Next, at 1709, the signal router sets appropriate switches to route pulse or pulse train delivery to appropriate output channels and then sends a trigger signal to the pulse generator. Upon reception of the trigger signal, the pulse generator generates the desired pulse or pulse train and outputs it to the signal router, from where the output is routed to appropriate device electrodes, at 1711. In embodiments, the signal router can include current measurement circuitry to check for proper pulse delivery. In such embodiments, if incorrect or unexpected measurements are seen, at 1713, the signal router reports an error and opens all switches to stop further output delivery, at 1715. Otherwise, at 1717, the signal router opens all switches and checks to see if more pulses or pulse trains are required, for example, to other channel or electrode pairings. If further pulse delivery is required or desired, the process returns to 1709, where the signal router updates its signal routing switches suitably and sends another trigger signal to the pulse generator. The process continues in this manner until the check at 1717 indicates that waveform delivery is complete. Upon completion, at 1721, the process ends and in embodiments, the system can indicate to the user via a user interface that waveform delivery has been successfully completed.

FIG. 23 is a flow chart of an example method 1800 of delivering a pulse sequence with a system including a pulse generator, a signal router, and a plurality of electrode channels including a plurality of electrodes coupled thereto. The method 1800 may be performed by any of the systems and/or devices described herein, including, for example, pulse generator 1400 and router 1402. All such variants should be considered to be within the scope of this disclosure.

The method 1800 may include establishing (and/or confirming) a communication between the pulse generator and the signal router. The signal router may be configured to set switches of the plurality of electrode channels (e.g., as shown in FIGS. 15, 16, and 22) to connect one or more sets of electrodes of the plurality of electrodes to the pulse generator such that the pulse generator can deliver a plurality of pulses (e.g., biphasic) to the one or more sets of electrodes. In some embodiments, the method 1800 may include sending a signal (e.g., a first signal) from the generator to the router, the signal including information of one or more parameters of the plurality of pulses and pulse sequence information (e.g., similar to that shown in FIGS. 18-21), at 1802. In some embodiments, the one or more parameters of the plurality of pulses may include one or more pulse widths (e.g., a duration of the positive phase and/or the negative phase of the biphasic pulse) and an inter-phase delay (e.g., a duration between the positive phase and the negative phase of the biphasic pulse). In some embodiments, the pulse sequence information can include information on delays between pulses (e.g., a pulse-to-pulse delay or a packet delay). In some embodiments, the signal may be sent from the generator to the signal router each time a pulse sequence is selected (e.g., by a user and/or based on the selection of a procedure). In some embodiments, the one or more parameters of the pulses may be constant across the pulse sequence. For example, the pulse width, pulse amplitude, and/or inter-phase delay of the pulses may remain constant throughout a pulse sequence. In some embodiments, the one or more parameters of the pulses may vary across the pulse sequence. In some embodiments, the signal generator (or pulse generator) may send multiple signals including the pulse parameter and pulse sequence information, such as, for example, sending a signal before each pulse indicating the one or more parameters of that pulse and/or delay to a next pulse. The signal router can then use that information to appropriate set the switches of the electrode channels, as described below. For example, the signal may be sent to the signal router at the base of each pulse.

In some embodiments, the method 1800 may include, prior to each pulse, sending a signal (e.g., a second signal) from the pulse generator to the signal router assigning a subset of electrodes from the plurality of electrodes to be activated for that pulse, at 1804. Optionally, in some embodiments, this additional signal from the generator to the router may include information such as pulse parameters (e.g., pulse width, inter-phase delay) and/or delay-to-next-pulse information (e.g., a pulse-to-pulse delay or a packet delay). In some embodiments, the first signal, sent at 1802, and the second signal, sent at 1804, may be sent separately. For example, the second signal may be sent after the first signal. In some embodiments, the first signal and the second signal may be sent together or simultaneously. In some embodiments, a single signal including the assignment of the subset of electrodes, pulse parameters, and/or delay-to-next pulse information can be sent from the generator to the router. Upon receiving the assignment of the subset of electrodes for a particular pulse, the signal router may be configured to set one or more switches to electrically couple the set of electrodes for that pulse to the generator, at 1806. In some embodiments, where only one set of electrodes is being energized in each pulse, and therefore the same electrodes are being assigned to each pulse, information assigning subsets of electrodes to each pulse is not sent.

In embodiments, the pulse sequence information such as the information in the pulse tables (e.g., as depicted in FIGS. 18-21) can be duplicated in the pulse generator and the router, or divided between the pulse generator and the router. For example, in implementations using a pulse table, the pulse generator can retain or make use of the timing information in the pulse table (e.g., the pulse-to-pulse delays), while the router can retain or make use of the sequence of electrode pairings. In embodiments, once a device/electrode selection is made from the pulse generator, automatically by device detection and/or user selection, an appropriate pulse table identification is sent to the router (e.g., in a signal). The router selects the appropriate pulse table with electrode pairing sequence information. The pulse generator includes a memory with matching pulse table information including pulse parameters and pulse-to-pulse delays. Once the pulse generator is ready to deliver ablation, it sends an acknowledgement (e.g., signal) to the router that then sets electrode switches in accordance with the electrode pairing sequence in the pulse table and informs the generator that the correct switch settings are in place. The pulse generator then sends an ablation pulse along with pulse on/pulse off information (e.g., in a signal) to the router, which delivers the ablation pulse to the appropriate electrodes. The router then sends an acknowledgement (e.g., signal) to the generator and is ready to reset the switches according to the next entry in the pulse table in readiness for the next pulse, and the generator delivers the next pulse with suitable timing from the pulse table timing information. In this manner all the pulses in the pulse sequence are delivered to the appropriate electrode pairings.

At 1808, the method 1800 may optionally include sending an acknowledgment signal or a trigger signal from the signal router to the generator, e.g., indicating the one or more switches have been set such that the assigned electrodes are coupled to the pulse generator and/or to trigger the pulse generator to generate the pulse. At 1810, the method may include generating a pulse at the generator, e.g., in response to the generator receiving the trigger signal from the router. At 1812, the signal router may adjust the switches according to the pulse width and, for a biphasic pulse, the inter-phase delay of the biphasic pulse. For example, the signal router may be configured to (i) set the switches such that a positive duration of the biphasic pulse may be delivered, (ii) open the switches for a duration corresponding to the inter-phase delay, and (iii) reverse the switches such that a negative duration of the biphasic pulse may be delivered. In some embodiments, after the pulse is complete, the method may include sending a confirmation (e.g., from the signal router to the generator) that the pulse has been delivered. At 1816, the method 1800 may include opening the switches for a duration corresponding to the pulse-to-pulse delay for the pulse. In some embodiments, 1804-1814 may be repeated for each pulse in the pulse sequence until a total number of pulses in the pulse sequence have been delivered. In some embodiments, one or more parameters (e.g., pulse width, inter-phase delay, the subset of electrodes, and/or the pulse-to-pulse delay) may vary with each iteration of 1804-1814.

In an embodiment where only a pulse generator is required, e.g., for a fixed or limited signal routing, the pulse generator can suitably direct the opening and closing of switches for pulse train delivery. It should be noted that an appropriate user interface can comprise any of a variety of such interfaces that are known in the art, including a computer monitor, touch screen, mouse, wand, joystick, voice activation, foot switch, gesture recognition etc. without limitations.

Pulsed waveform delivery as disclosed herein can be applied for pulsed field ablation delivery in unipolar (also called monopolar) mode between one or more device electrodes and a reference electrode patch on the subject surface, or in embodiments, subsets of device electrodes can be used as a bipolar electrode pair for bipolar pulsed field ablation delivery. Application of a pulsed field ablation waveform to the electrodes results in the generation of an electric field and, depending on the tissue irreversible electroporation threshold, a lesion zone with a boundary determined by the threshold value of the electric field is generated as a result of ablation. In embodiments, if a larger treatment volume or region is desired, the medical device can be moved to and positioned at a different location, and therapy can be delivered at the new location. In embodiments, more than one ablation or waveform delivery can be performed at a given anatomical location as convenient for the application.

The systems, devices, and methods described herein can be embodied in one or more embodiments, as set forth below.

Embodiment 1: A system for ablation therapy delivery comprising a pulse generator coupled to an ablation device, the pulse generator configured to generate a voltage pulse train of biphasic pulses, each biphasic pulse comprising a positive pulse and a negative pulse, an inter-phase delay separating the positive pulse and the negative pulse, successive biphasic pulses separated by a pulse-to-pulse delay, with a subset of successive pulse-to-pulse delays in the pulse train comprising an increasing sequence of delays.

Embodiment 2: A system for ablation therapy delivery comprising a pulse generator coupled to an ablation device, the pulse generator configured to generate a voltage pulse train of biphasic pulses, each biphasic pulse comprising a positive pulse and a negative pulse, an inter-phase delay separating the positive pulse and the negative pulse, successive biphasic pulses separated by a pulse-to-pulse delay, with a subset of successive pulse-to-pulse delays in the pulse train comprising a decreasing sequence of delays.

Embodiment 3: A system for ablation therapy delivery comprising a pulse generator coupled to an ablation device, the pulse generator configured to generate a voltage pulse train of biphasic pulses, each biphasic pulse comprising a positive pulse and a negative pulse, an inter-phase delay separating the positive pulse and the negative pulse, successive biphasic pulses separated by a pulse-to-pulse delay, with a first subset of successive pulse-to-pulse delays in the pulse train comprising an increasing sequence of delays, and with a second subset of successive pulse-to-pulse delays in the pulse train comprising a decreasing sequence of delays.

Embodiment 4: The system of Embodiment 1, where the increasing sequence of successive pulse-to-pulse delays follows at least an arithmetic progression.

Embodiment 5: The system of Embodiment 2, where the decreasing sequence of successive pulse-to-pulse delays follows at least an arithmetic progression.

Embodiment 6: The system of Embodiment 3, where the increasing sequence of delays in the first subset of successive pulse-to-pulse delays in the pulse train follows at least an arithmetic progression, and the decreasing sequence of delays in the second subset of successive pulse-to-pulse delays in the pulse train follows at least an arithmetic progression.

Embodiment 7: The system of Embodiment 1, where the increasing sequence of successive pulse-to-pulse delays follows at least a geometric progression.

Embodiment 8: The system of Embodiment 2, where the decreasing sequence of successive pulse-to-pulse delays follows at least a geometric progression.

Embodiment 9: The system of Embodiment 3, where the increasing sequence of delays in the first subset of successive pulse-to-pulse delays in the pulse train follows at least a geometric progression, and the decreasing sequence of delays in the second subset of successive pulse-to-pulse delays in the pulse train follows at least a geometric progression.

Embodiment 10: The system of Embodiment 1, where the increasing sequence of pulse-to-pulse delays in the pulse train comprise at least one third of the total number of pulse-to-pulse delays in the pulse train.

Embodiment 11: The system of Embodiment 2, where the decreasing sequence of pulse-to-pulse delays in the pulse train comprise at least one third of the total number of pulse-to-pulse delays in the pulse train.

Embodiment 12: The system of Embodiment 3, where the pulse train comprises up to 150 complete biphasic pulses.

Embodiment 13: The system of Embodiment 1, where the positive and negative pulse of each biphasic pulse comprise substantially rectangular pulses.

Embodiment 14: The system of Embodiment 2, where the positive and negative pulse of each biphasic pulse comprise substantially rectangular pulses.

Embodiment 15: The system of Embodiment 1, where the positive and negative pulse of each biphasic pulse comprise approximately trapezoidal pulses, with the pulse width of a positive or negative phase being the width or duration for which the voltage value is at least 70% of the maximum amplitude value.

Embodiment 16: The system of Embodiment 2, where the positive and negative pulse of each biphasic pulse comprise trapezoidal pulses, with the pulse width of a positive or negative phase being the width or duration for which the voltage value is at least 70% of the maximum amplitude value.

Embodiment 17: The system of Embodiment 13, where the inter-phase delay is at least three times the pulse width.

Embodiment 18: The system of Embodiment 14, where the inter-phase delay is at least three times the pulse width.

Embodiment 19: The system of Embodiment 15, where the inter-phase delay is at least three times the pulse width.

Embodiment 20: The system of Embodiment 16, where the inter-phase delay is at least three times the pulse width.

Embodiment 21: The system of Embodiment 3, where the inter-phase delay is at least 5 microseconds.

Embodiment 22: The system of Embodiment 3, where the pulse width is in the range between approximately 0.5 microseconds and approximately 150 microseconds.

Embodiment 23: A system for ablation therapy delivery comprising a pulse generator coupled to an ablation device, the pulse generator configured to generate a multiplicity of voltage pulse packets with successive packets separated by a series of packet delays, each pulse packet comprising a voltage pulse train of biphasic pulses, each biphasic pulse comprising a positive pulse and a negative pulse, an inter-phase delay separating the positive pulse and the negative pulse, successive biphasic pulses separated by a pulse-to-pulse delay, with a subset of successive pulse-to-pulse delays in the pulse train comprising an increasing sequence of delays.

Embodiment 24: A system for ablation therapy delivery comprising a pulse generator coupled to an ablation device, the pulse generator configured to generate a multiplicity of voltage pulse packets with successive packets separated by a series of packet delays, each pulse packet comprising a voltage pulse train of biphasic pulses, each biphasic pulse comprising a positive pulse and a negative pulse, an inter-phase delay separating the positive pulse and the negative pulse, successive biphasic pulses separated by a pulse-to-pulse delay, with a subset of successive pulse-to-pulse delays in the pulse train comprising a decreasing sequence of delays.

Embodiment 25: A system for ablation therapy delivery comprising a pulse generator coupled to an ablation device, the pulse generator configured to generate a multiplicity of voltage pulse packets with successive packets separated by a series of packet delays, each pulse packet comprising a voltage pulse train of biphasic pulses, each biphasic pulse comprising a positive pulse and a negative pulse, an inter-phase delay separating the positive pulse and the negative pulse, successive biphasic pulses separated by a pulse-to-pulse delay, with a first subset of successive pulse-to-pulse delays in the pulse train comprising an increasing sequence of delays, and with a second subset of successive pulse-to-pulse delays in the pulse train comprising a decreasing sequence of delays.

Embodiment 26: The system of Embodiment 23, with the multiplicity of pulse packets comprising up to 20 packets.

Embodiment 27: The system of Embodiment 25, with each packet delay lying in the range between approximately 300 milliseconds and approximately 12 seconds.

Embodiment 28: The system of Embodiment 25, with the voltage amplitude of the pulses lying in the range between approximately 300 Volts and 10,000 Volts.

Embodiment 29: A system for ablation therapy delivery comprising a pulse generator coupled to a router with activated switches for channel routing to electrode sets, with an ablation device with a multiplicity of electrodes coupled to the router, with a communication channel between the pulse generator and router for communicating a trigger signal from the router to the pulse generator, and with distinct subsets of router switches for channel routings to distinct electrode sets activated during at least two successive trigger signals, wherein the pulse generator generates a biphasic voltage pulse comprising a positive pulse and a negative pulse upon receiving the trigger signal, with an inter-phase delay separating the positive pulse and the negative pulse, and with the generated pulse being passed through the router to electrodes on the ablation device.

Embodiment 30: A system for ablation therapy delivery comprising a pulse generator coupled to a router with activated switches for channel routing to electrode sets, with an ablation device with a multiplicity of electrodes coupled to the router, with a communication channel between the pulse generator and router for communicating a trigger signal from the router to the pulse generator, and with distinct subsets of router switches for channel routings to distinct electrode sets activated during at least two successive trigger signals, wherein the pulse generator generates a biphasic voltage pulse train of biphasic pulses upon receiving the trigger signal, each biphasic pulse comprising a positive pulse and a negative pulse, an inter-phase delay separating the positive pulse and the negative pulse, with successive biphasic pulses separated by a pulse-to-pulse delay, with a subset of successive pulse-to-pulse delays in the pulse train for pulses applied to at least one electrode set comprising an increasing sequence of delays.

Embodiment 31: A system for ablation therapy delivery comprising a pulse generator coupled to a router with activated switches for channel routing to electrode sets, with an ablation device with a multiplicity of electrodes coupled to the router, with a communication channel between the pulse generator and router for communicating a trigger signal from the router to the pulse generator, and with distinct subsets of router switches for channel routings to distinct electrode sets activated during at least two successive trigger signals, wherein the pulse generator generates a biphasic voltage pulse train of biphasic pulses upon receiving the trigger signal, each biphasic pulse comprising a positive pulse and a negative pulse, an inter-phase delay separating the positive pulse and the negative pulse, with successive biphasic pulses separated by a pulse-to-pulse delay, with a subset of successive pulse-to-pulse delays in the pulse train for pulses applied to at least one electrode set comprising a decreasing sequence of delays.

Embodiment 32: A method comprising generating, using a pulse generator coupled to an ablation device, a voltage pulse train including a plurality of biphasic pulses, each biphasic pulse of the plurality of biphasic pulses including a positive pulse, a negative pulse, and an inter-phase delay separating the positive pulse and the negative pulse, successive biphasic pulses of the plurality of biphasic pulses being separating by a pulse-to-pulse delay such that the plurality of biphasic pulses is separated by a plurality of pulse-to-pulse delays, and the plurality of pulse-to-pulse delays including an increasing sequence of pulse-to-pulse delays including a subset of successive pulse-to-pulse delays for pulses applied to at least one electrode set that progressively increase.

Embodiment 33: The method of embodiment 32, wherein the plurality of pulse-to-pulse delays further includes a decreasing sequence of pulse-to-pulse delays for pulses applied to at least one electrode set including a subset of successive pulse-to-pulse delays that progressively decrease.

Embodiment 34: The method of embodiment 32-33, wherein the positive and negative pulses of each biphasic pulse of the plurality of biphasic pulses includes substantially rectangular pulses.

Embodiment 34: The method of embodiment 34, wherein the inter-phase delay of each biphasic pulse of the plurality of biphasic pulses is at least three times a pulse width of the positive and negative pulses of each biphasic pulse of the plurality of biphasic pulses.

Embodiment 35: The method of embodiment 32-33, wherein the positive and negative pulses of each biphasic pulse of the plurality of biphasic pulses includes substantially trapezoidal pulses, and each positive or negative pulse has a pulse width that corresponds to a width or duration for which a voltage value of the positive or negative pulse is at least about 70% of a maximum amplitude value of the positive or negative pulse.

Embodiment 36: The method of embodiment 35, wherein the inter-phase delay of each biphasic pulse of the plurality of biphasic pulses is at least three times the pulse width of the positive and negative pulses of each biphasic pulse of the plurality of biphasic pulses.

Embodiment 37: The method of embodiment 32-36, wherein the inter-phase delay of each biphasic pulse of the plurality of biphasic pulses is at least about five microseconds.

Embodiment 38: The method of embodiment 32-37, wherein a pulse width of each positive or negative pulse of the plurality of biphasic pulses is between about 0.5 microseconds and about 150 microseconds.

Embodiment 39: The method of embodiment 32-38, wherein a maximum amplitude of each positive or negative pulse of the plurality of biphasic pulses is between about 300 Volts and about 10,000 Volts.

While specific examples have been provided in the various figures for example and illustrative purposes, it should be clear that variants such as different numbers of pulses, pulse packets, electrode sets and the like are included in the present disclosure. While specific medical devices are illustrated in the disclosure as examples, it should be apparent that a variety of other types of medical devices targeting a variety of clinical applications can be used with the system, methods and waveforms described herein. For example, various types of medical devices with electrodes in the forms of needles, rings, balloons, solid tips, curved geometries, and so on can be used to deliver therapy with the apparatus, method and waveforms described herein to treat several types of benign or cancerous tumors, deliver ablation for renal or other denervation, or to ablate a variety of types of soft tissue. The electrodes of the catheter device described herein or other medical devices generally can be attached or connected to an electrical conductor that attaches to a cable or connector cable for delivery of electrical energy from the generator system, e.g., for the delivery of high voltage pulsed field ablation waveforms.

In embodiments, the ablation can generate an electric field not sufficient to cause irreversible electroporation but sufficient to cause reversible electroporation, wherein cell membranes in the zone of reversible electroporation are permeabilized to permit the passage of drug molecules or other therapeutic agents into the cells, for example, to treat cancer. It is understood that the term "ablation" herein includes both the reversible or temporary permeabilization of cell membranes as well as irreversible or permanent permeabilization of cell membranes. Depending on the clinical application, for example tumor treatment, it may be desired to destroy targeted cells for therapy, or to temporarily permeabilize cell membranes for the passage of therapeutic agents such as drug molecules or viral vectors carrying gene therapies or other such agents known in the art for tumor treatment.

The voltage amplitude of the waveforms described herein can range from approximately 300 V to approximately 10,000V depending on the application, including all values and ranges therebetween. The pulse widths of the waveforms can range from approximately 0.5 microseconds to approximately 150 microseconds, including all values and ranges therebetween. The inter-phase delay can range from approximately 5 microseconds to approximately 3 milliseconds, including all values and ranges therebetween. The pulse-to-pulse delay can range from approximately 15 microseconds to approximately 500 milliseconds, including all values and ranges therebetween, and the packet delay can range from 300 milliseconds to approximately 12 seconds, including all values and ranges therebetween.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within +10% of the recited value. For example, in some instances, "about 100 [units]" may mean within +10% of 100 (e.g., from 90 to 110). The terms "about" and "approximately" may be used interchangeably.

The invention claimed is:

1. A method, comprising:
generating, using a pulse generator configured to be coupled to an ablation device, a voltage pulse train, the voltage pulse train including:
a plurality of biphasic pulses, each biphasic pulse of the plurality of biphasic pulses including a positive phase, a negative phase, and an inter-phase delay separating the positive phase and the negative phase,
successive biphasic pulses of the plurality of biphasic pulses being separated by a pulse-to-pulse delay such that the plurality of biphasic pulses is separated by a plurality of pulse-to-pulse delays, and
the plurality of pulse-to-pulse delays including an increasing sequence of pulse-to-pulse delays including a subset of successive pulse-to-pulse delays that progressively increase and a decreasing sequence of pulse-to-pulse delays including a subset of successive pulse-to-pulse delays that progressively decrease, wherein the decreasing sequence of pulse-to-pulse delays follows the increasing sequence of pulse-to-pulse delays or the increasing sequence of pulse-to-pulse delays follows the decreasing sequence of pulse-to-pulse delays; and
delivering the voltage pulse train to an electrode set of the ablation device to apply pulsed field ablation to tissue.

2. The method of claim 1, wherein at least one of (1) the increasing sequence of pulse-to-pulse delays increases according to at least an arithmetic progression or (2) the decreasing sequence of pulse-to-pulse delays decreases according to at least an arithmetic progression.

3. The method of claim 1, wherein at least one of (1) the increasing sequence of pulse-to-pulse delays increases according to at least a geometric progression or (2) the decreasing sequence of pulse-to-pulse delays decreases according to at least a geometric progression.

4. The method of claim 1 wherein the increasing sequence of pulse-to-pulse delays includes at least one third of a total number of the plurality of pulse-to-pulse delays.

5. The method of claim 1, wherein the decreasing sequence of pulse-to-pulse delays includes at least one third of a total number of the plurality of pulse-to-pulse delays.

6. The method of claim 1, wherein the plurality of biphasic pulses includes up to about one hundred biphasic pulses.

7. The method of claim 1, wherein the inter-phase delay of each biphasic pulse of the plurality of biphasic pulses is at least three times a width of the positive and negative phases of each biphasic pulse of the plurality of biphasic pulses.

8. The method of claim 7, wherein the positive and negative phases of each biphasic pulse of the plurality of biphasic pulses have substantially trapezoidal shapes, and each positive or negative phase has a width that corresponds to a width or duration for which a voltage value of the positive or negative phase is at least about 70% of a maximum amplitude value of the positive or negative phase.

9. The method of claim 7, wherein the positive and negative phase of each biphasic pulse of the plurality of biphasic pulses has substantially rectangular shape.

10. The method of claim 1, wherein the inter-phase delay of each biphasic pulse of the plurality of biphasic pulses is at least about five microseconds.

11. The method of claim 1, wherein a width of each positive or negative phase of the plurality of biphasic pulses is between about 0.5 microseconds and about 150 microseconds.

12. The method of claim 1, further comprising:

generating, using the pulse generator, a plurality of packets, each packet of the plurality of packets including a voltage pulse train, and successive packets of the plurality of packets being separated by a packet delay of a plurality of packet delays.

13. A method, comprising:

generating, using a pulse generator configured to be coupled to an ablation device, voltage pulse trains, each voltage pulse train including:

a plurality of biphasic pulses, each biphasic pulse of the plurality of biphasic pulses including a positive phase, a negative phase, and an inter-phase delay separating the positive phase and the negative phase, successive biphasic pulses of the plurality of biphasic pulses being separated by a pulse-to-pulse delay such that the plurality of biphasic pulses is separated by a plurality of pulse-to-pulse delays, and the plurality of pulse-to-pulse delays including at least one of (1) an increasing sequence of pulse-to-pulse delays including a subset of successive pulse-to-pulse delays that progressively increase or (2) a decreasing sequence of pulse-to-pulse delays including a subset of successive pulse-to-pulse delays that progressively decrease; and delivering the voltage pulse trains to a plurality of electrode sets of the ablation device to apply pulsed field ablation to tissue by interleaving the plurality of biphasic pulses of the voltage pulse train being delivered to a first electrode set of the plurality of electrode sets with at least the voltage pulse train being delivered to a second electrode set of the plurality of electrode sets.

14. The method of claim 13, wherein at least one of (1) the increasing sequence of pulse-to-pulse delays increases according to at least an arithmetic progression or (2) the decreasing sequence of pulse-to-pulse delays decreases according to at least an arithmetic progression.

15. The method of claim 13, wherein at least one of (1) the increasing sequence of pulse-to-pulse delays increases according to at least a geometric progression or (2) the decreasing sequence of pulse-to-pulse delays decreases according to at least a geometric progression.

16. The method of claim 13, wherein the increasing sequence of pulse-to-pulse delays includes at least one third of a total number of the plurality of pulse-to-pulse delays.

17. The method of claim 13, wherein the decreasing sequence of pulse-to-pulse delays includes at least one third of a total number of the plurality of pulse-to-pulse delays.

18. The method of claim 13, wherein the plurality of biphasic pulses includes up to about one hundred biphasic pulses.

19. The method of claim 13, wherein the inter-phase delay of each biphasic pulse of the plurality of biphasic pulses is at least three times a width of the positive and negative phases of each biphasic pulse of the plurality of biphasic pulses.

20. The method of claim 19, wherein the positive and negative phases of each biphasic pulse of the plurality of biphasic pulses have substantially trapezoidal shapes, and each positive or negative phase has a width that corresponds to a width or duration for which a voltage value of the positive or negative phase is at least about 70% of a maximum amplitude value of the positive or negative phase.

21. The method of claim 19, wherein the positive and negative phase of each biphasic pulse of the plurality of biphasic pulses has substantially rectangular shape.

22. The method of claim 13, wherein the inter-phase delay of each biphasic pulse of the plurality of biphasic pulses is at least about five microseconds.

23. The method of claim 13, wherein a width of each positive or negative phase of the plurality of biphasic pulses is between about 0.5 microseconds and about 150 microseconds.

24. The method of claim 13, wherein a maximum amplitude of each positive or negative phase of the plurality of biphasic pulses is between about 300 Volts and about 10,000 Volts.

25. The method of claim 13, further comprising:

generating, using the pulse generator, a plurality of packets, each packet of the plurality of packets including a voltage pulse train, and successive packets of the plurality of packets being separated by a packet delay of a plurality of packet delays.

26. The method of claim 25, wherein the plurality of packets includes up to about twenty packets.

27. The method of claim 25, wherein each packet delay of the plurality of packet delays is between about 300 milliseconds and about 12 seconds.

28. The method of claim 13, wherein the increasing sequence of pulse-to-pulse delays include a number of delays equal to that of the decreasing sequence of pulse-to-pulse delays.

29. The method of claim 13, wherein the first electrode set and the second electrode set share a common electrode.

30. The method of claim 13, further comprising:

setting, using a signal router, one or more switches and generating a series of trigger signals; and delivering, in response to the series of trigger signals, the plurality of biphasic pulses of the voltage pulse train being delivered to the first electrode set to the first electrode set and the plurality of biphasic pulses of the voltage pulse train being delivered to the second electrode set to the second electrode set.

* * * * *